(12) United States Patent
Xiao et al.

(10) Patent No.: US 11,647,671 B2
(45) Date of Patent: May 9, 2023

(54) COMPOUND AND ORGANIC ELECTRO-OPTICAL DEVICE CONTAINING THE SAME

(71) Applicants: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

(72) Inventors: Wenjing Xiao, Shanghai (CN); Wei Gao, Shanghai (CN); Lei Zhang, Shanghai (CN); Wenpeng Dai, Shanghai (CN); Quan Ran, Shanghai (CN); Jinghua Niu, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 380 days.

(21) Appl. No.: 17/006,932

(22) Filed: Aug. 31, 2020

(65) Prior Publication Data
US 2020/0395554 A1    Dec. 17, 2020

(30) Foreign Application Priority Data
May 15, 2020    (CN) .......................... 202010414303.3

(51) Int. Cl.
| | | |
|---|---|---|
| *C07D 307/93* | (2006.01) | |
| *C07D 405/10* | (2006.01) | |
| *C07D 407/10* | (2006.01) | |
| *C07D 409/14* | (2006.01) | |
| *C07D 471/04* | (2006.01) | |
| *C07F 5/02* | (2006.01) | |
| *C07F 9/53* | (2006.01) | |
| *H01L 51/00* | (2006.01) | |
| *H01L 51/50* | (2006.01) | |

(52) U.S. Cl.
CPC ........ *H01L 51/0073* (2013.01); *C07D 307/93* (2013.01); *C07D 405/10* (2013.01); *C07D 407/10* (2013.01); *C07D 409/14* (2013.01); *C07D 471/04* (2013.01); *C07F 5/027* (2013.01); *C07F 9/5325* (2013.01); *H01L 51/0067* (2013.01); *H01L 51/0072* (2013.01); *H01L 51/0074* (2013.01); *H01L 51/5072* (2013.01); *H01L 51/5096* (2013.01)

(58) Field of Classification Search
CPC .................................................. C07D 307/93
See application file for complete search history.

(56) References Cited

FOREIGN PATENT DOCUMENTS

| CN | 110256428 A | 9/2019 | |
|---|---|---|---|
| WO | 2011037429 A2 | 3/2011 | |
| WO | WO-2011037429 A2 * | 3/2011 | ........... C07C 309/36 |

OTHER PUBLICATIONS

Computer-generated English-language translation of WO2011/037429A2 to Kim et al.*

* cited by examiner

*Primary Examiner* — Vu A Nguyen
(74) *Attorney, Agent, or Firm* — Kilpatrick Townsend & Stockton LLP

(57) ABSTRACT

Provided are a compound and an organic electro-optical device containing the same. The compound has a structure represented by Formula I. The organic electro-optical device comprises an anode, a cathode, and at least one organic thin film layer located between the cathode and the anode. The molecule of the compound provided by the present disclosure has higher rigidity, a large conjugated system, a deeper LUMO energy level, a higher triplet energy level and good molecular stability, and is not easy to crystallize, and thus the compound can be used as an electron transport material or a hole blocking material of the organic electro-optical device, facilitating the reduction of the turn-on voltage of the device, the improvement of current efficiency and the increase of service life.

13 Claims, No Drawings

COMPOUND AND ORGANIC ELECTRO-OPTICAL DEVICE CONTAINING THE SAME

CROSS-REFERENCE TO RELATED APPLICATIONS

The application claims the benefit of the earlier filing date of C.N. Patent Application No. 202010414303.3, filed on May 15, 2020, the contents of which are incorporated by reference herein in its entirety.

FIELD

The present disclosure belongs to the field of organic electro-optical materials, and relates to a compound and an organic electro-optical device containing the same.

BACKGROUND

Organic light emitting diode (OLED) is a kind of light emitting device based on organic light-emitting materials, and is widely concerned due to its advantages such as efficient light emitting, simple production process, large area flexibility, etc. Currently, OLED devices basically meet the requirements of small and medium-sized displays, and have been widely applied in the field of flat-panel display and illumination, such as instrumentation, high-end smart-phones, televisions, etc.

OLED is a carrier double-injection light-emitting device, and its light-emitting mechanism is: driven by external electric fields, carriers (electrons and holes) are injected from the cathode and anode, respectively, then meet, recombine and generate excitons in the organic light-emitting layer, and release and transfer energy to the organic light-emitting material to initiate a transition of the organic light-emitting material from the ground state to the excited state and the excited state radiation releases energy, resulting in electroluminescence.

Besides the necessary light-emitting layer, the OLED device generally contains one or more of the following auxiliary layers: a hole injection layer, a hole transport layer, an electron blocking layer, a hole blocking layer, an electron transport layer or an electron injection layer, for adjusting the injection and transport of electrons and holes. Therefore, the luminescence efficiency, service time and other properties of the OLED device are not only directly affected by the material of the organic light-emitting layer, but also are related to the injection, transport, recombination of electrons and holes as well as the degree of the quantitative balance between the two.

The main function of the electron transport layer is to transport electrons. The electron mobility of the electron transport layer directly affects the number of electrons recombined with holes, and thus the electron transport layer has an important influence on the luminescence performance of the OLED device. Generally, the material of the electron transport layer is required to have a deeper LUMO energy level and a higher electron mobility to facilitate the injection and transport of electrons, and also required to have higher stability, and a higher triplet energy level to block excitons and prevent the excitons from entering the auxiliary layers to cause a decrease in luminescence efficiency.

However, the current research on the OLED device is still in the development stage. There are fewer types of good electron transport materials, and more electron transport materials with higher performances are still to be developed.

SUMMARY

Embodiments of the present disclosure are to provide a compound and an organic electro-optical device containing the same. The molecule of the compound has higher rigidity, a large conjugated system, a deeper LUMO energy level, a higher triplet energy level and good molecular stability, and is not easy to crystallize. Thus the compound can be used as an electron transport material or a hole blocking material of the organic electro-optical device, facilitating the reduction of the turn-on voltage of the device, the improvement of current efficiency and the increase of service life.

In a first aspect, the present disclosure provides a compound. The compound has a structure represented by Formula I:

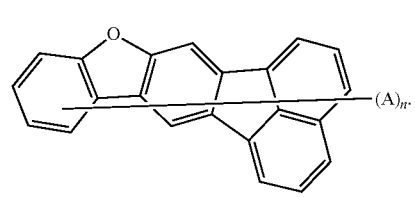

Formula I

In Formula I, A is an electron acceptor group; n represents the number of A, and is an integer of 1 to 3 (which, for example, may be 1, 2 or 3).

In a second aspect, the present disclosure provides an organic electro-optical device. The organic electro-optical device comprises an anode, a cathode and at least one organic thin film layer located between the anode and the cathode.

The at least one organic thin film layer is one selected from the group consisting of a hole injection layer, a hole transport layer, an electron blocking layer, a light emitting layer, a hole blocking layer, an electron transport layer, an electron injection layer, and a combination of at least two selected therefrom, and comprises a light emitting layer.

At least one of the organic thin film layers comprises at least one of the compounds described in the first aspect.

Compared with the related art, the present disclosure has the following beneficial effects:

The molecule of the compound provided by the present disclosure has higher rigidity, a large conjugated system, a deeper LUMO energy level (<−1.7 eV), a higher triplet energy level (>2.0 eV) and good molecular stability, and is not easy to crystallize. Thus the compound can be used as an electron transport material or a hole blocking material of the organic electro-optical device, reducing the turn-on voltage of the device, improving current efficiency and service life.

DETAILED DESCRIPTION

In a first aspect, the present disclosure provides a compound. The compound has a structure represented by Formula I:

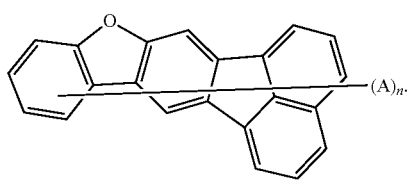

Formula I

In Formula I, A is an electron acceptor group.

n represents the number of A, and is an integer of 1 to 3 (which, for example, may be 1, 2 or 3).

It is to be noted that the electron donor is opposite to the electron acceptor, and in the present disclosure, that A is an electron acceptor group refers to that A is an electron acceptor group with respect to the structure of acenaphtho dibenzofuran

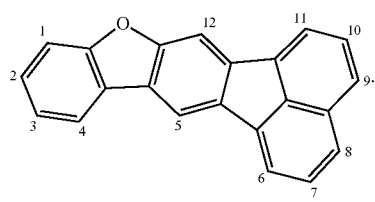

In the present disclosure, the substitution position of the A group represented by the structure of Formula I is any n positions in 1-12 positions of the structure of acenaphtho dibenzofuran.

The compound provided by the present disclosure can be used as an electron transport material of an organic electro-optical device. The molecule of the compound has a larger conjugated structure, which facilitates the transport of carriers, and a deeper LUMO energy level, which facilities the injection of electrons and the improvement of electron mobility of a device. The molecule of the compound has strong rigidity, large molecular torque and is easy to vibrate, and a higher triplet energy level, which is favorable for blocking excitons of the light emitting layer and limiting the excitons within the light emitting layer, improving the luminescence efficiency of the device. The molecular of the compound has strong rigidity and high glass transition temperature $T_g$, and is not easy to crystallize, which is favorable for vapor deposition film formation and ensures the stability of a film, increasing the service life of the device.

In one embodiment of the present disclosure, the compound has a structure represented by Formula II:

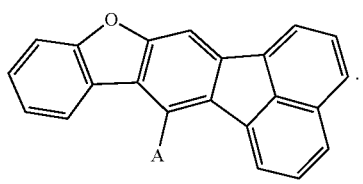

Formula II

The group A of the compound represented by Formula II is located at the 5 position of the acenaphtho dibenzofuran ring. On the one hand, the substitution activity of this position is higher than that of other positions, and thus the compound can be prepared more easily. On the other hand, the molecular steric resistance is larger at this position and the molecule is distorted, which facilitates the further improvement of the triplet energy level and the luminescence efficiency.

In one embodiment of the present disclosure, A is any one selected from the group consisting of a cyano-containing electron acceptor group, a nitrogen heterocycle-containing electron acceptor group, a sulfone-containing electron acceptor group, a carbonyl-containing electron acceptor group, a phosphinyloxy-containing electron acceptor group and a boron-containing electron acceptor group.

In one embodiment of the present disclosure, the cyano-containing electron acceptor group is any one selected from the group consisting of the following groups:

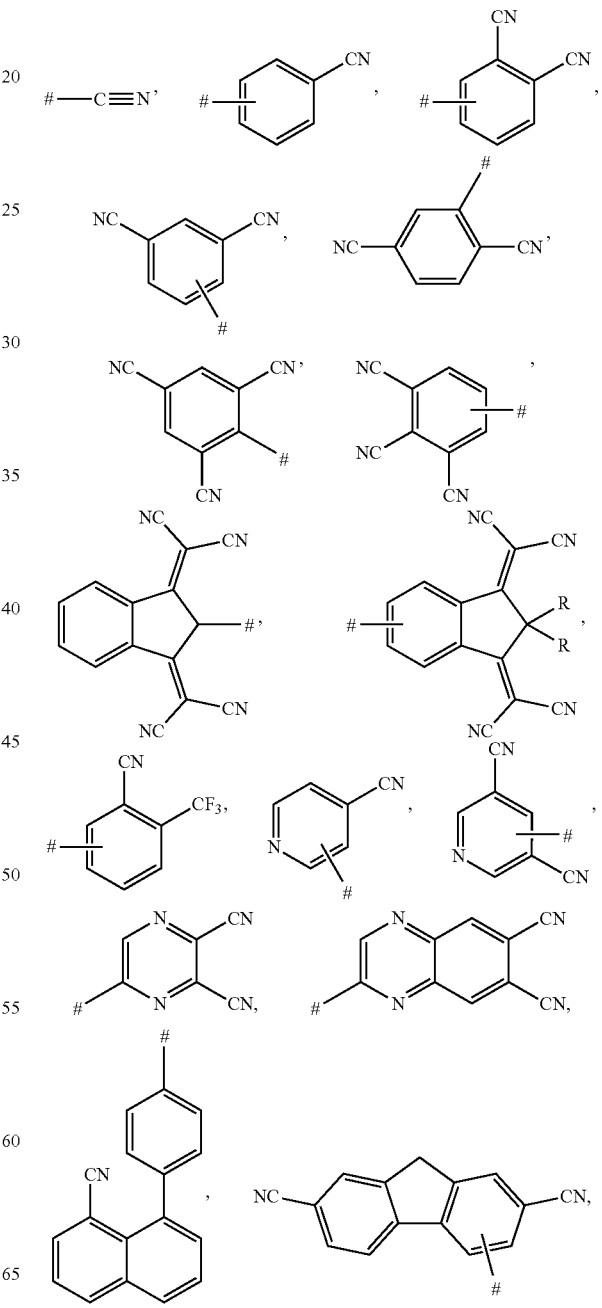

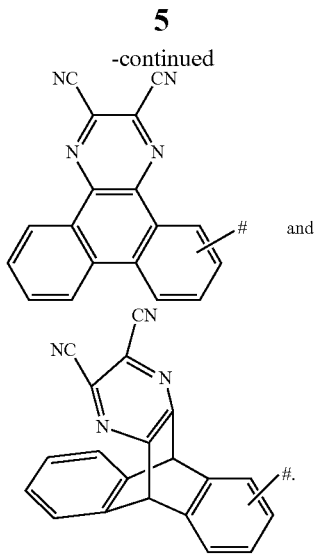

In the above groups, R is any one selected from the group consisting of a hydrogen atom, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkyl, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkoxy, $C_6$-$C_{30}$ (which, for example, may be $C_6$, $C_{10}$, $C_{12}$, $C_{18}$, $C_{24}$, $C_{28}$ or $C_{30}$) aryl and $C_2$-$C_{30}$ (which, for example, may be $C_2$, $C_3$, $C_4$, $C_5$, $C_8$, $C_{10}$, $C_{12}$, $C_{15}$, $C_{18}$, $C_{21}$, $C_{24}$, $C_{28}$ or $C_{30}$) heteroaryl, and #represents a linkage position of groups.

In one embodiment of the present disclosure, the nitrogen heterocycle-containing electron acceptor group is any one selected from the group consisting of the following groups:

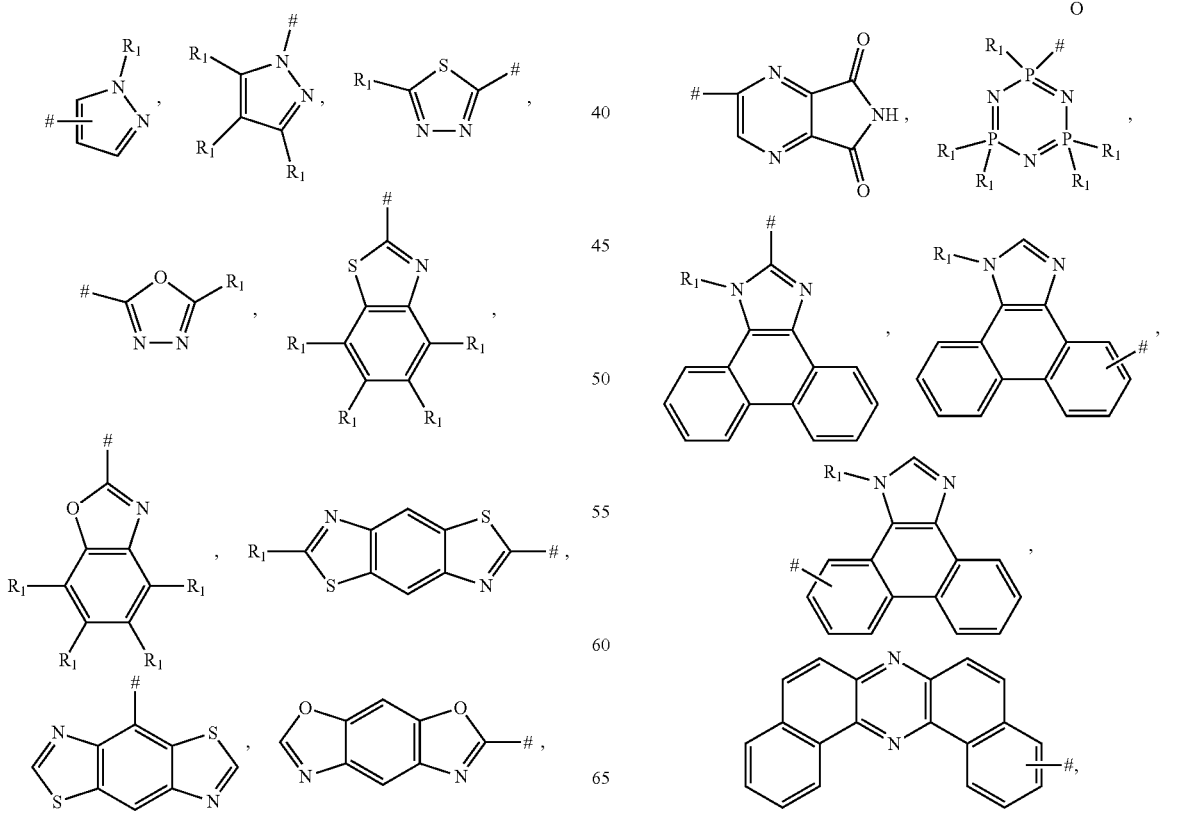

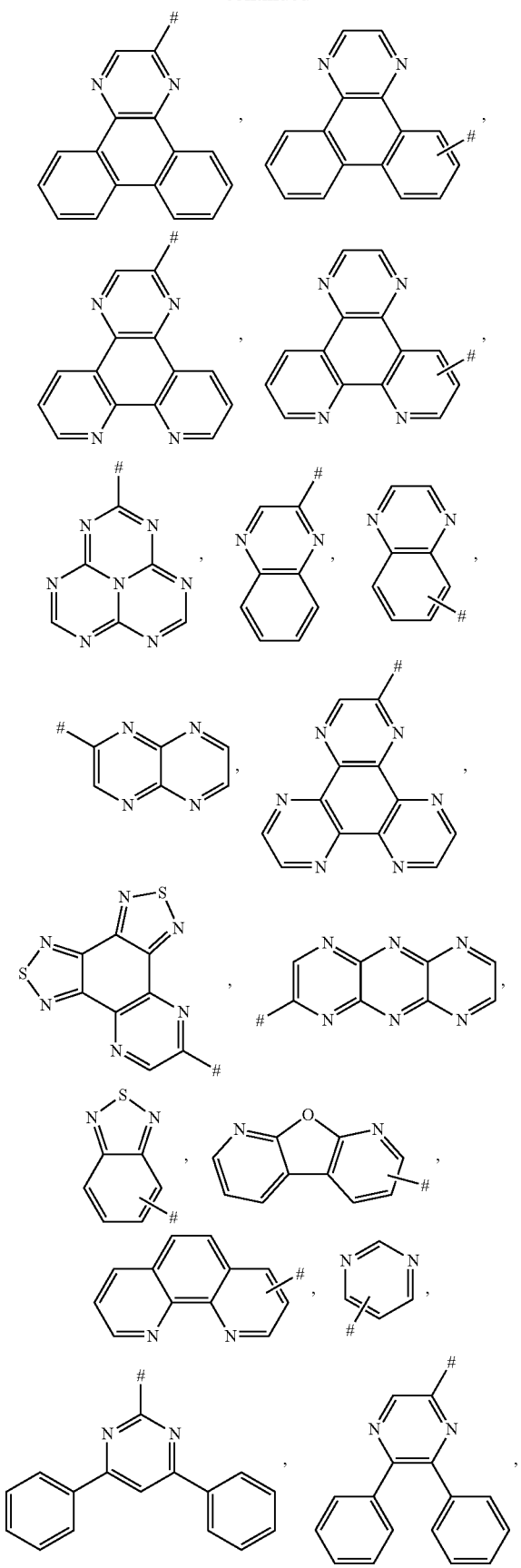

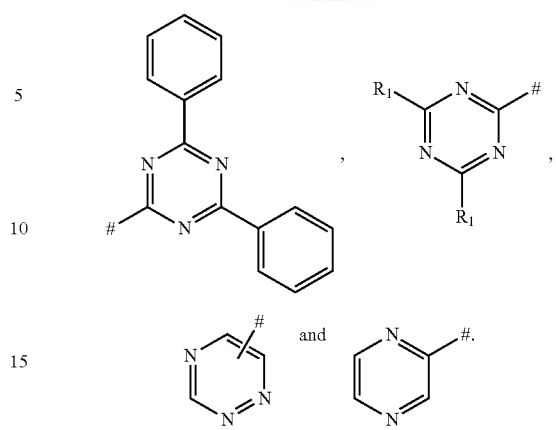

In the above groups, $R_1$ is any one selected from the group consisting of $C_1$-$C_{20}$ (which, for example, may be $C_1$, $C_3$, $C_5$, $C_8$, $C_{10}$, $C_{12}$, $C_{15}$, $C_{18}$ or $C_{20}$) alkyl, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkoxy, $C_6$-$C_{30}$ (which, for example, may be $C_6$, $C_{10}$, $C_{12}$, $C_{18}$, $C_{24}$, $C_{28}$ or $C_{30}$) aryl and $C_2$-$C_{30}$ (which, for example, may be $C_2$, $C_3$, $C_4$, $C_5$, $C_8$, $C_{10}$, $C_{12}$, $C_{15}$, $C_{18}$, $C_{21}$, $C_{24}$, $C_{28}$ or $C_{30}$) heteroaryl, and #represents a linkage position of groups.

In one embodiment of the present disclosure, the sulfone-containing electron acceptor group is any one selected from the group consisting of the following groups:

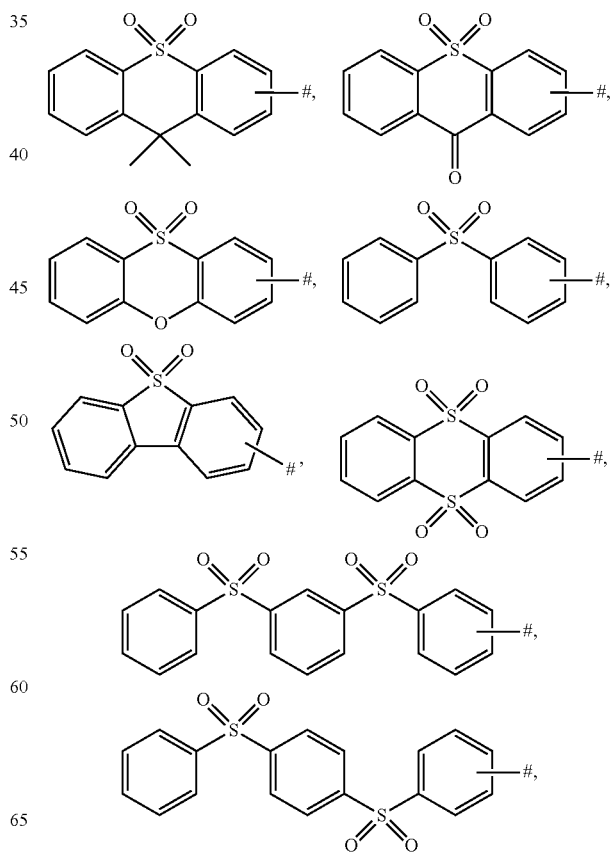

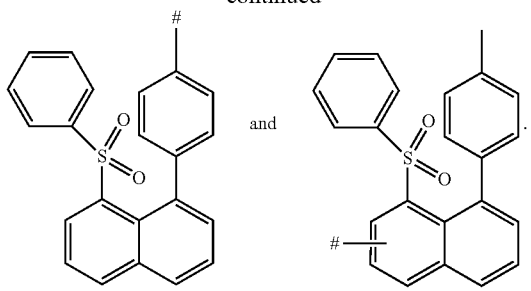 and 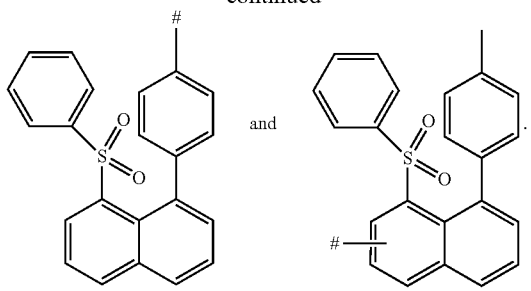.
In the above groups, # represents a linkage position of groups.
In one embodiment of the present disclosure, the carbonyl-containing electron acceptor group is any one selected from the group consisting of the following groups:
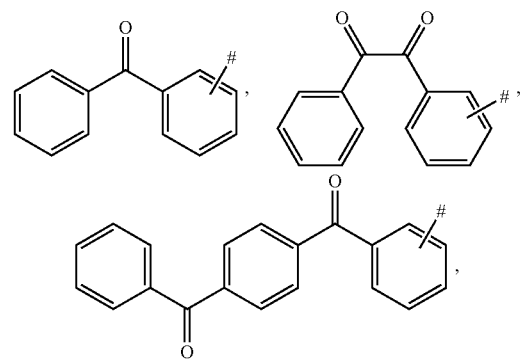
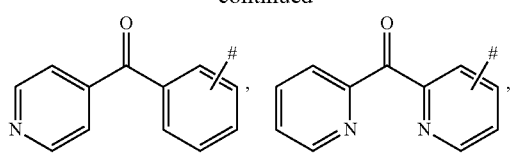
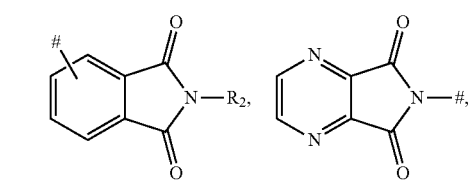
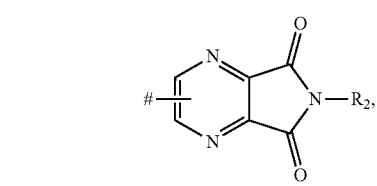
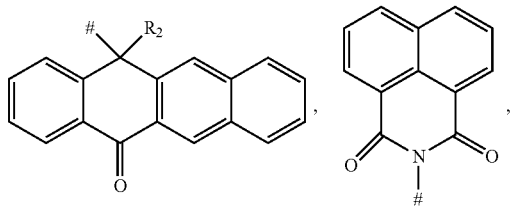
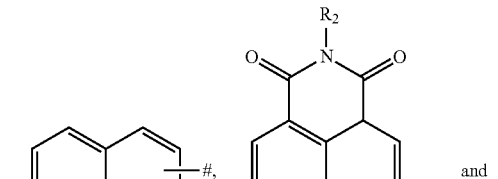
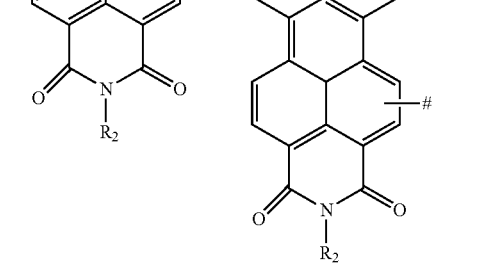 and -continued

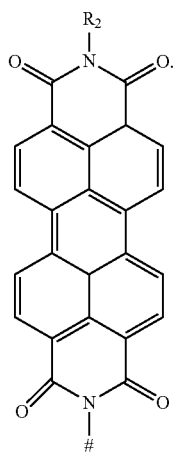

In the above groups, $R_2$ is any one selected from the group consisting of $C_1$-$C_{20}$ (which, for example, may be $C_1$, $C_3$, $C_5$, $C_8$, $C_{10}$, $C_{12}$, $C_{15}$, $C_{18}$ or $C_{20}$) alkyl, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkoxy, $C_6$-$C_{30}$ (which, for example, may be $C_6$, $C_{10}$, $C_{12}$, $C_{18}$, $C_{24}$, $C_{28}$ or $C_{30}$) aryl and $C_2$-$C_{30}$ (which, for example, may be $C_2$, $C_3$, $C_4$, $C_5$, $C_8$, $C_{10}$, $C_{12}$, $C_{15}$, $C_{18}$, $C_{21}$, $C_{24}$, $C_{28}$ or $C_{30}$) heteroaryl, and #represents a linkage position of groups.

In one embodiment of the present disclosure, the phosphinyloxy-containing electron acceptor group is any one selected from the group consisting of the following groups:

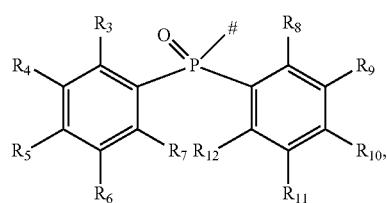

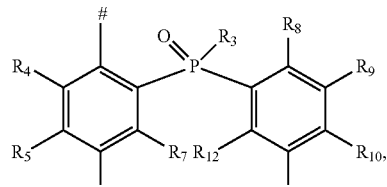

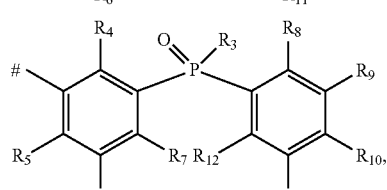

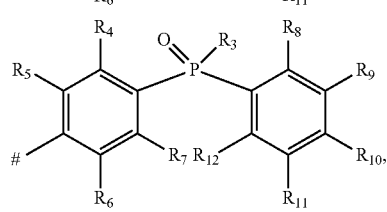

-continued

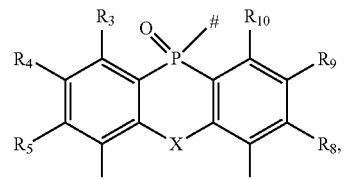

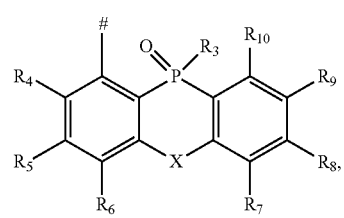

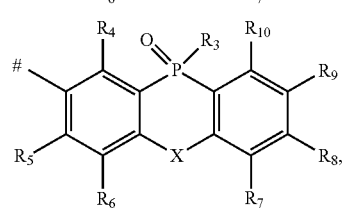

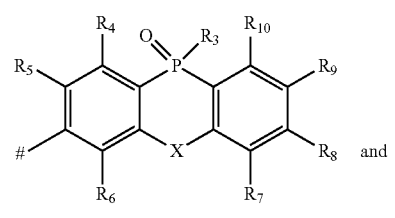

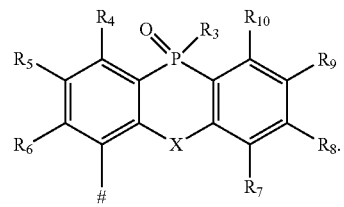

In the above groups, X is O, S, $R_3$ to $R_{12}$ are each independently any one selected from the group consisting of a hydrogen atom, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkyl, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkoxy, $C_6$-$C_{30}$ (which, for example, may be $C_6$, $C_{10}$, $C_{12}$, $C_{18}$, $C_{24}$, $C_{28}$ or $C_{30}$) aryl and $C_2$-$C_{30}$ (which, for example, may be $C_2$, $C_3$, $C_4$, $C_5$, $C_8$, $C_{10}$, $C_{12}$, $C_{15}$, $C_{18}$, $C_{21}$, $C_{24}$, $C_{28}$ or $C_{30}$) heteroaryl, $R_{13}$ is any one selected from the group consisting of $C_6$-$C_{30}$ (which, for example, may be $C_6$, $C_{10}$, $C_{12}$, $C_{18}$, $C_{24}$, $C_{28}$ or $C_{30}$) aryl and $C_2$-$C_{30}$ (which, for example, may be $C_2$, $C_3$, $C_4$, $C_5$, $C_8$, $C_{10}$, $C_{12}$, $C_{15}$, $C_{18}$, $C_{21}$, $C_{24}$, $C_{28}$ or $C_{30}$) heteroaryl, and #represents a linkage position of groups.

In one embodiment of the present disclosure, the boron-containing electron acceptor group is any one selected from the group consisting of the following groups:

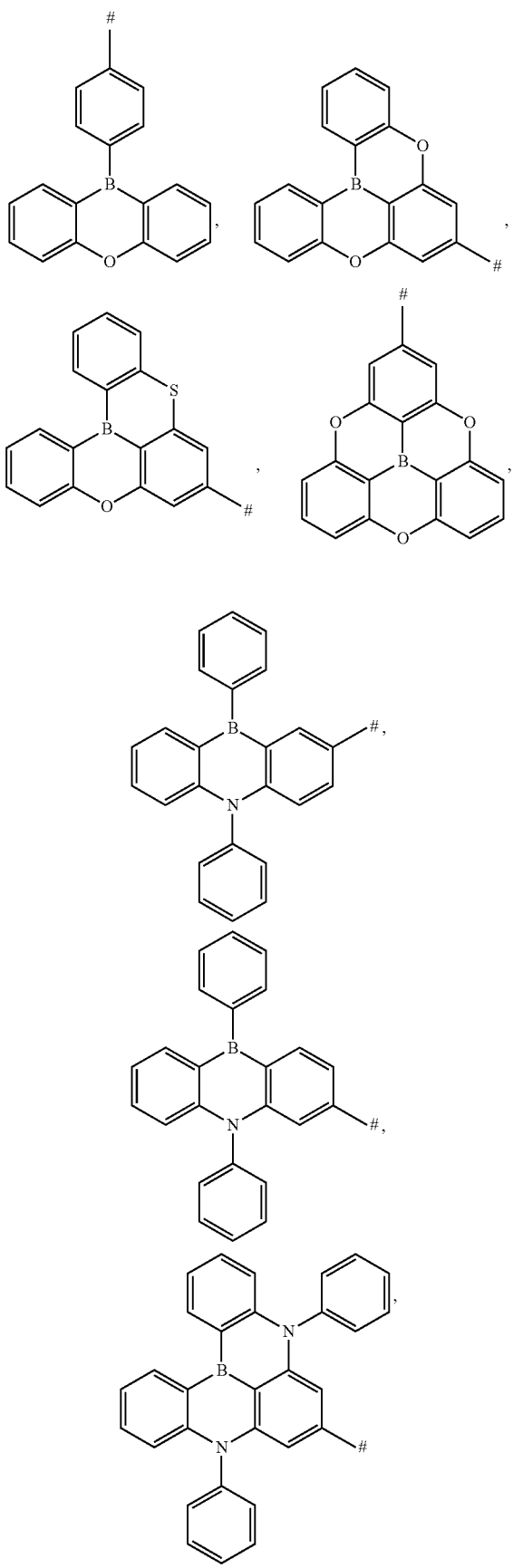

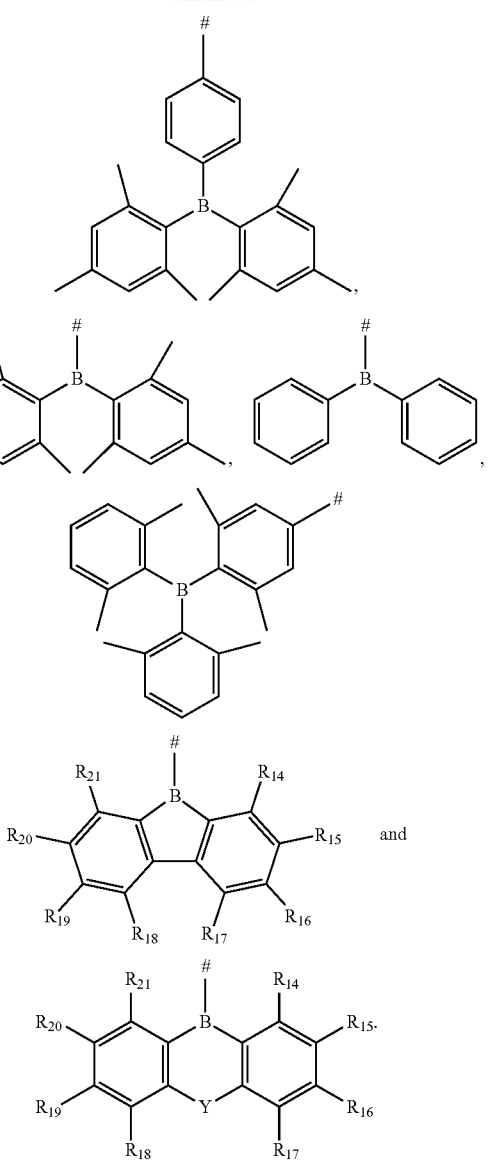

In the above groups, Y is O, S,

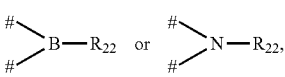

$R_{14}$ to $R_{22}$ are each independently any one selected from the group consisting of a hydrogen atom, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkyl, $C_1$-$C_{20}$ (which, for example, may be $C_1$, $C_3$, $C_5$, $C_8$, $C_{10}$, $C_{12}$, $C_{15}$, $C_{18}$ or $C_{20}$) alkoxy, $C_6$-$C_{30}$ (which, for example, may be $C_6$, $C_{10}$, $C_{12}$, $C_{18}$, $C_{24}$, $C_{28}$ or $C_{30}$) aryl and $C_2$-$C_{30}$ (which, for example, may be $C_2$, $C_3$, $C_4$, $C_5$, $C_8$, $C_{10}$, $C_{12}$, $C_{15}$, $C_{18}$, $C_{21}$, $C_{24}$, $C_{28}$ or $C_{30}$) heteroaryl, and #represents a linkage position of groups.

In one embodiment of the present disclosure, the compound is any one selected from the group consisting of the following compounds P1 to P97:

P1
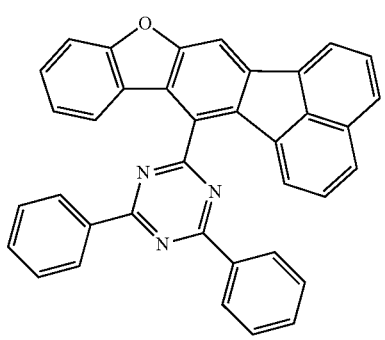
P2
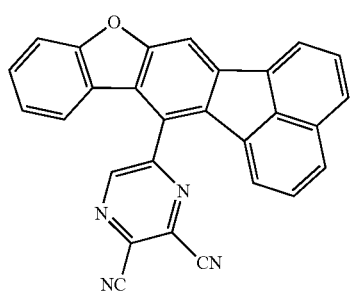
P3
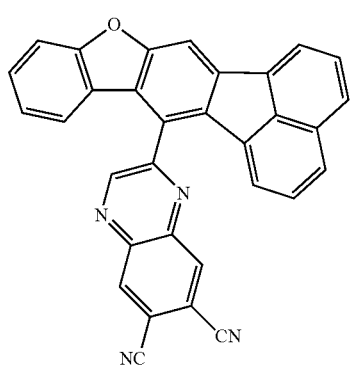
P4
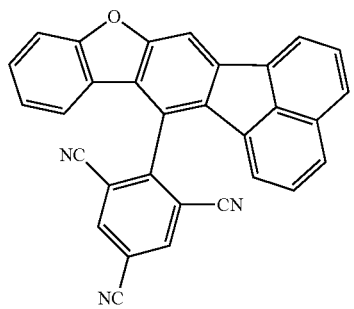
P5
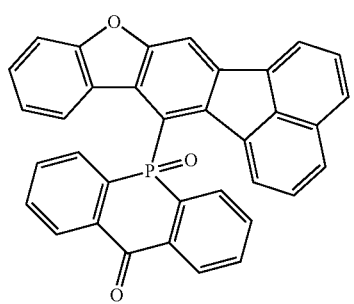
P6
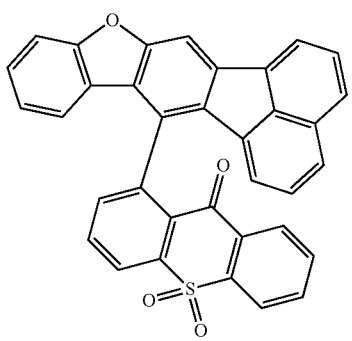
P7
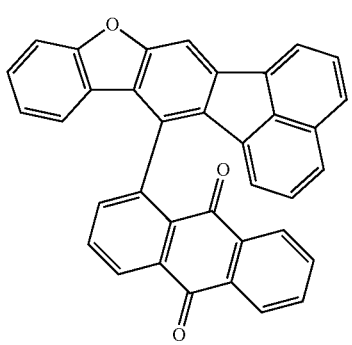
P8
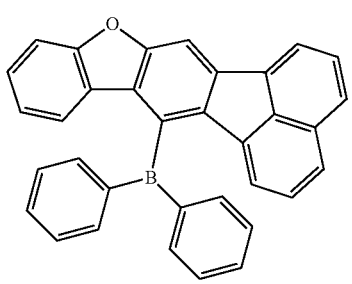
P9
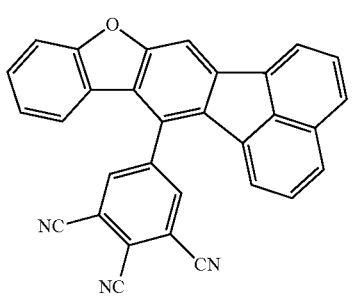
P10
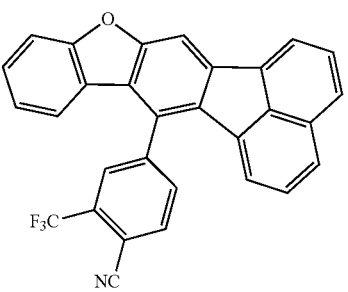

P11 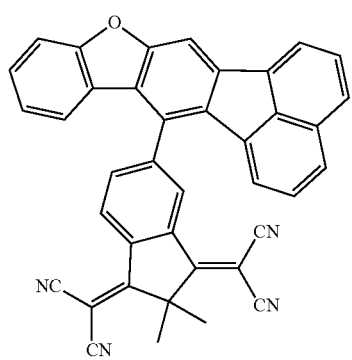
P12 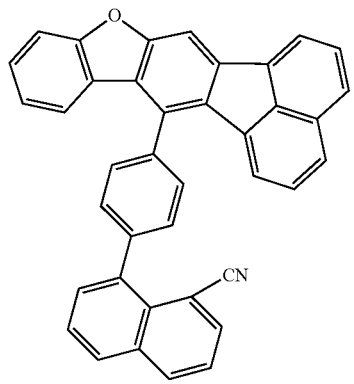
P13 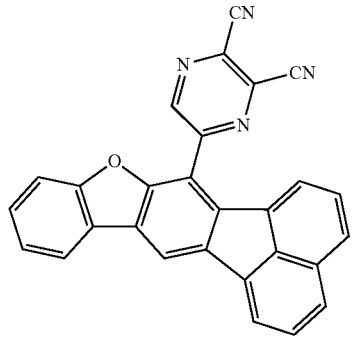
P14 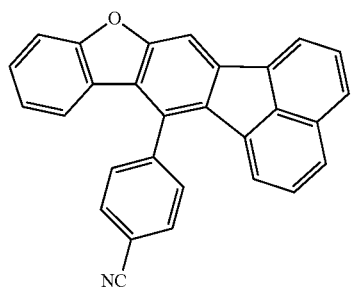
P15 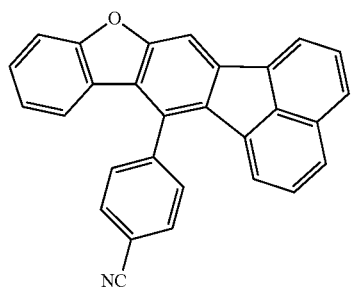
P16 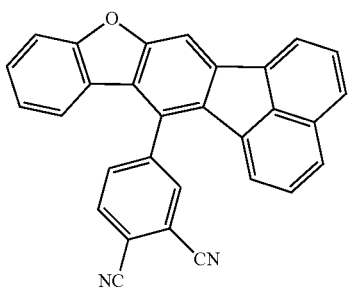
P17 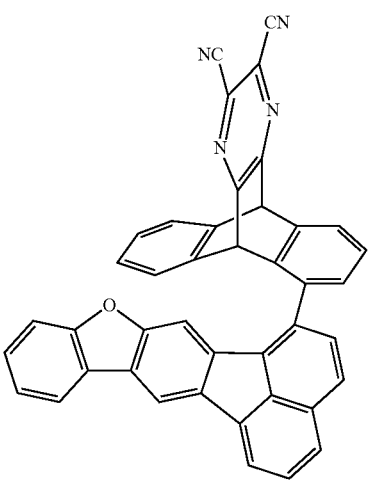
P18 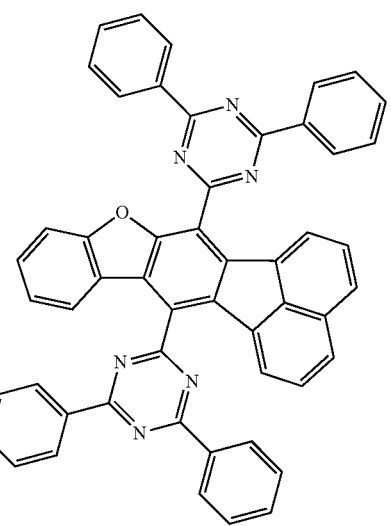

P19 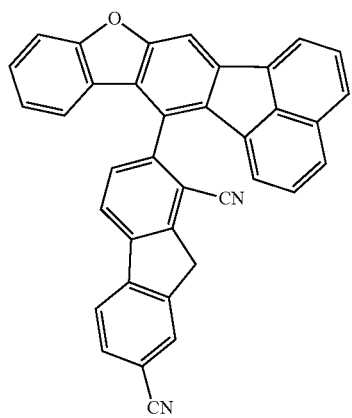
P23 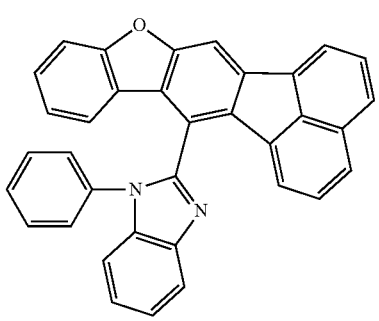
P24 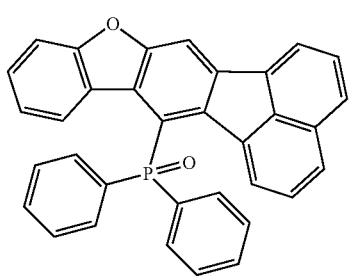
P20 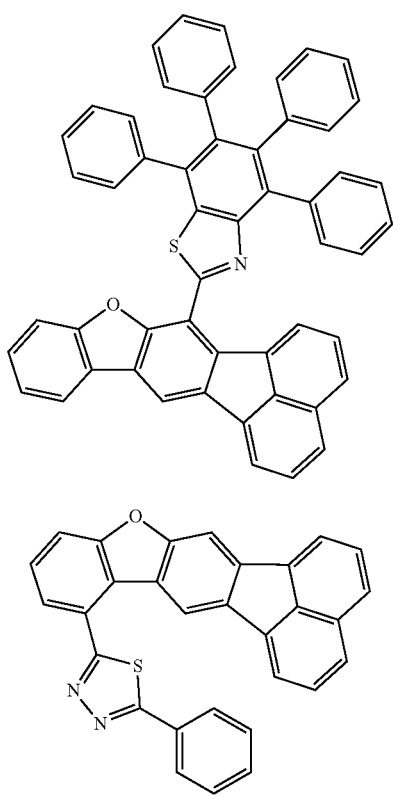
P25 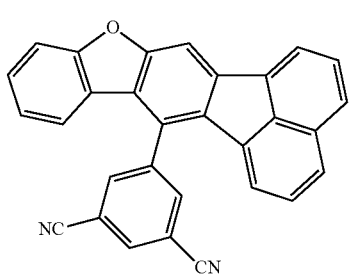
P26 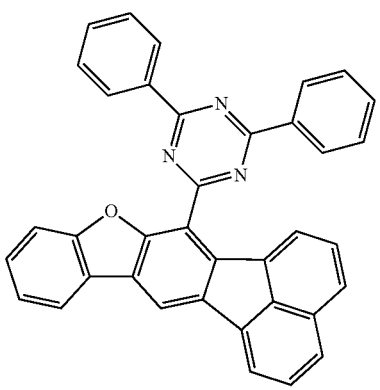
P21 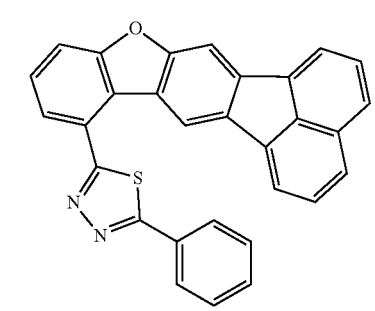
P22 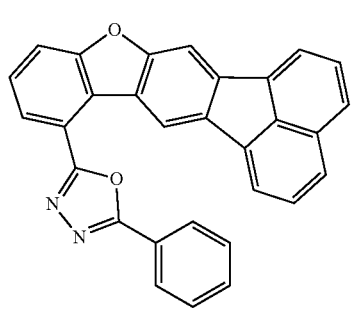
P27 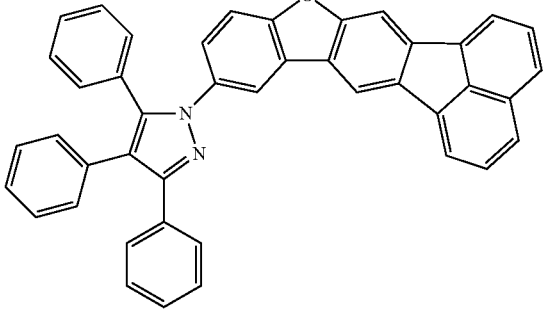

-continued
P28
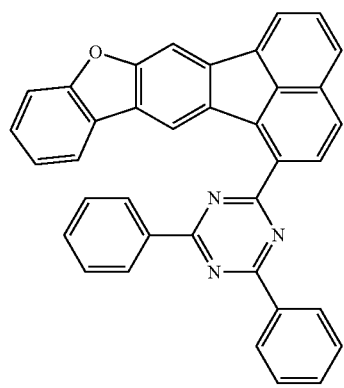
P29
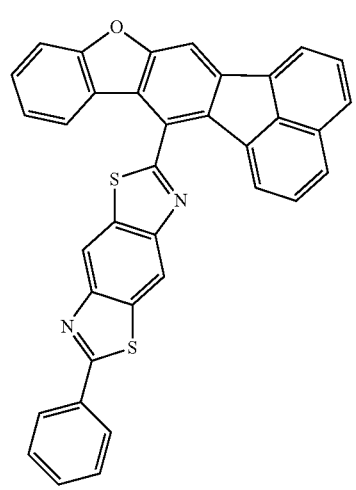
P30
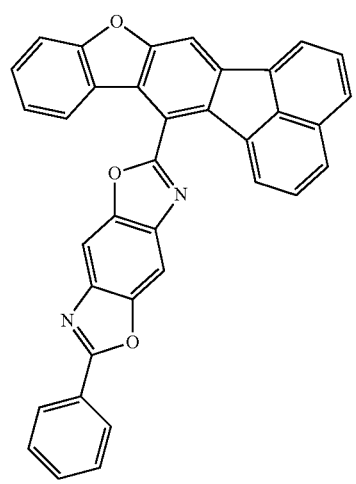
P31
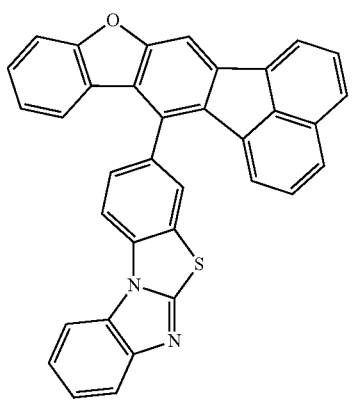
P32
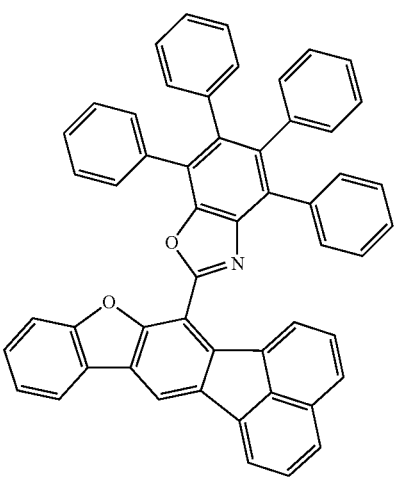
P33
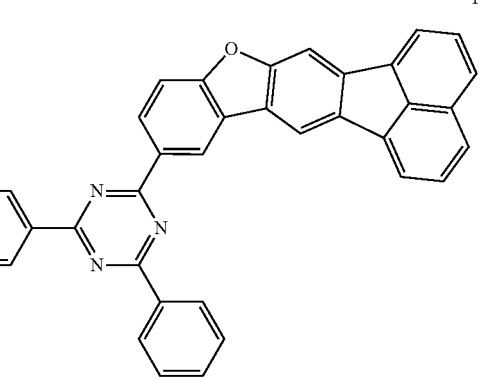
P34
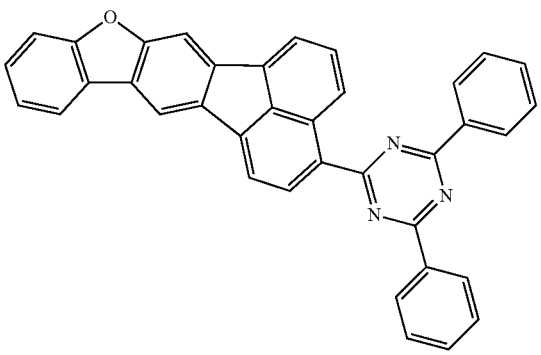

P35
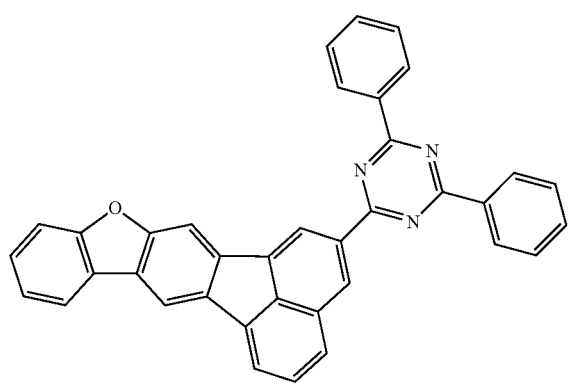
P36
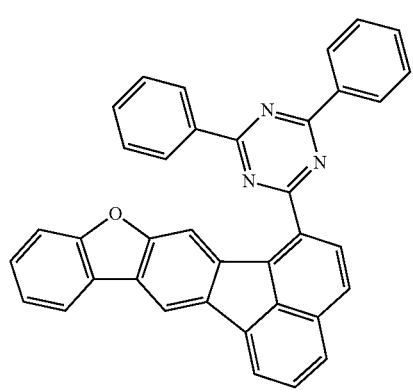
P37
P38
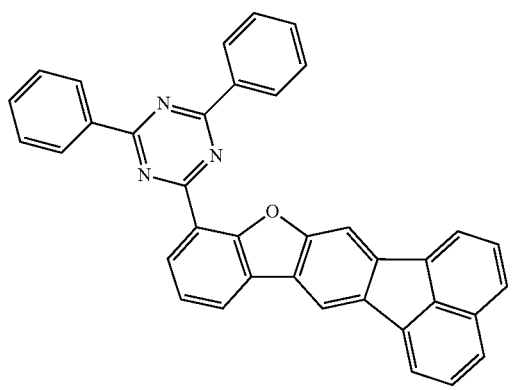
P39
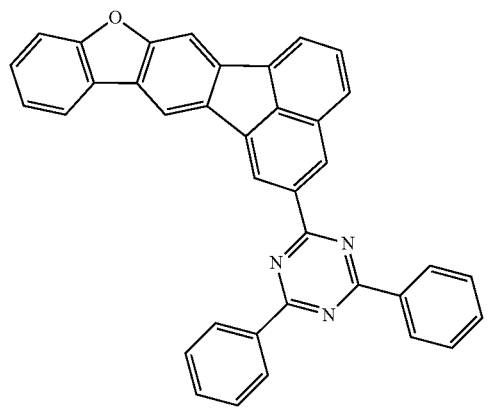
P44
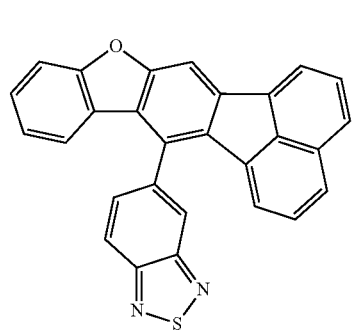
P45
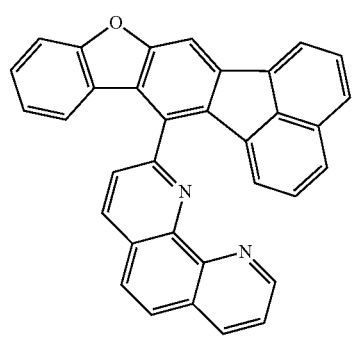
P46
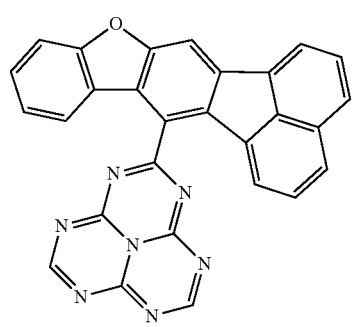

P47
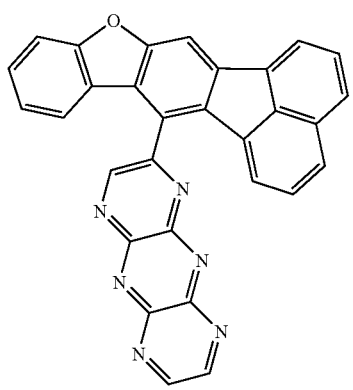
P48
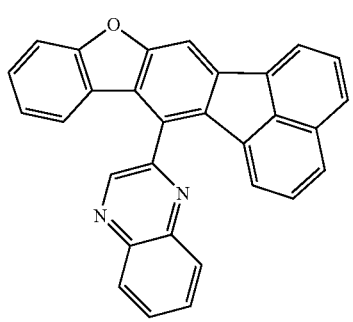
P49
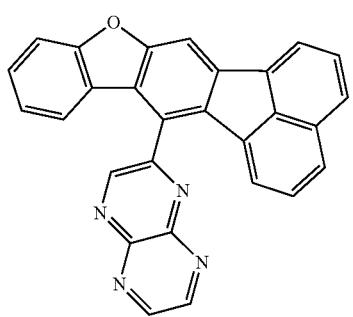
P50
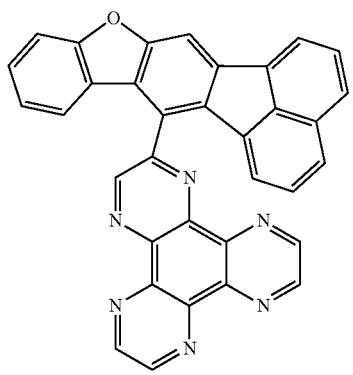
P51
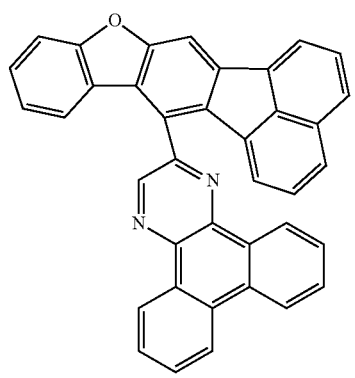
P52
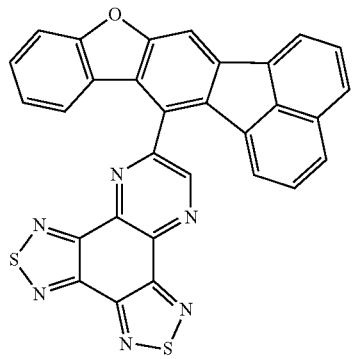
P53
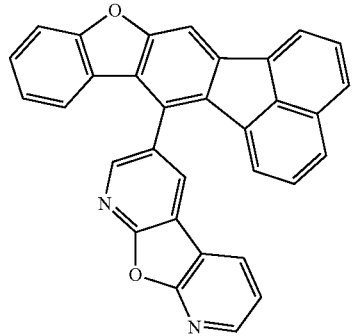
P54
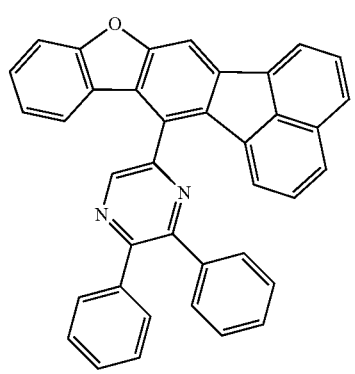

-continued
P55
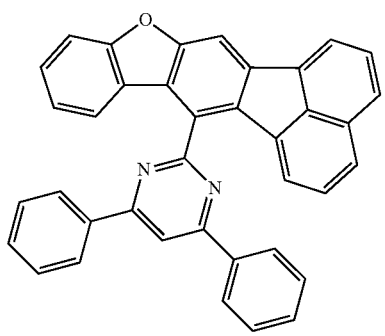
P56
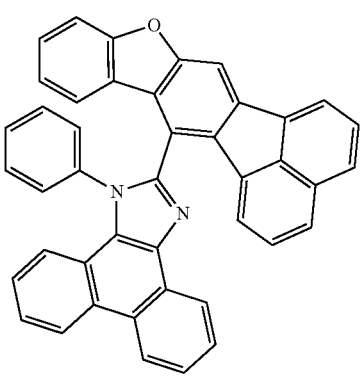
P57
P58
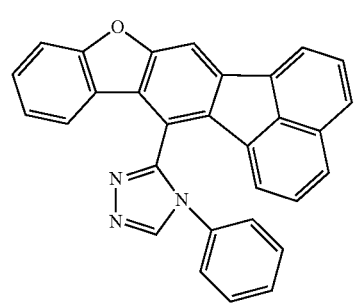
-continued
P59
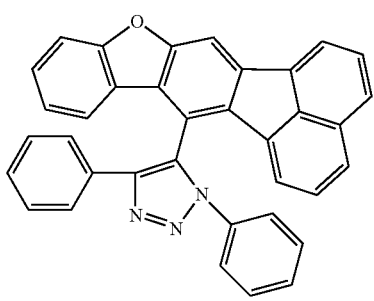
P60
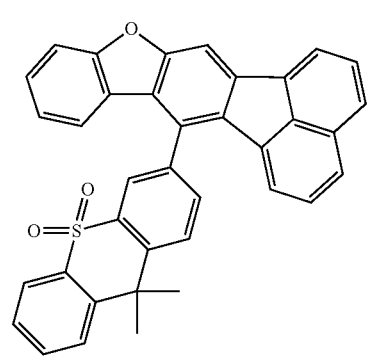
P61
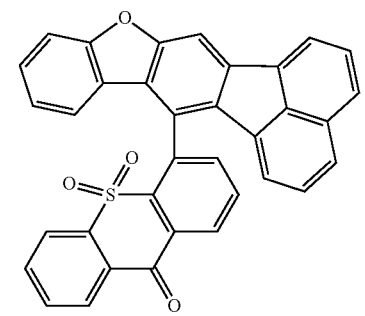
P62

-continued
P63
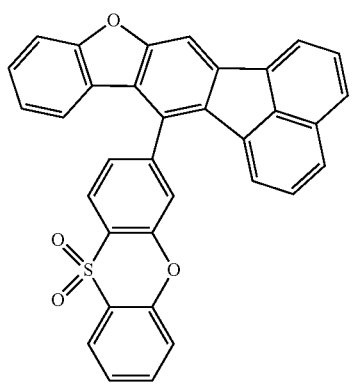
P64
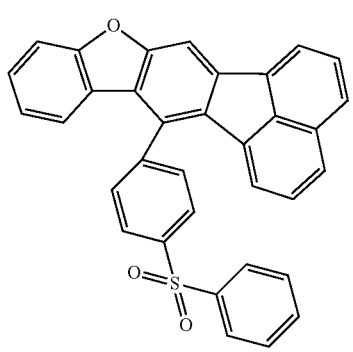
P65
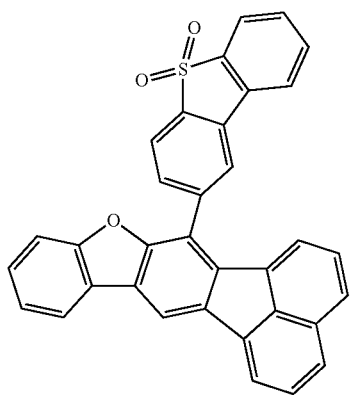
P66
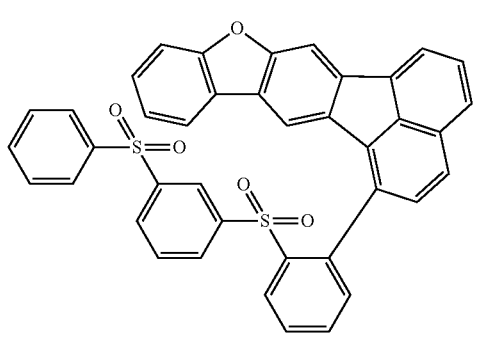
-continued
P67
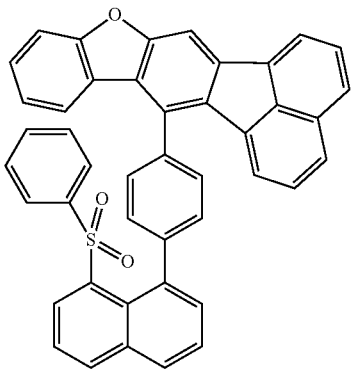
P68
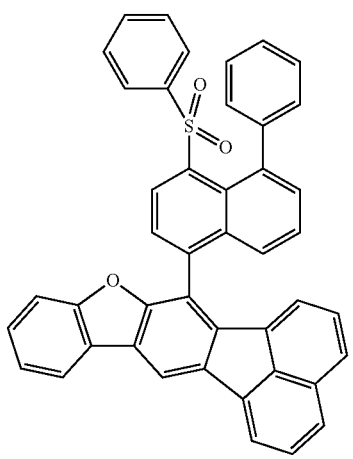
P69
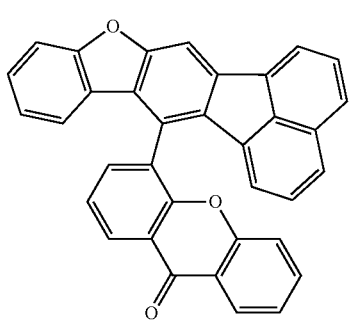
P70
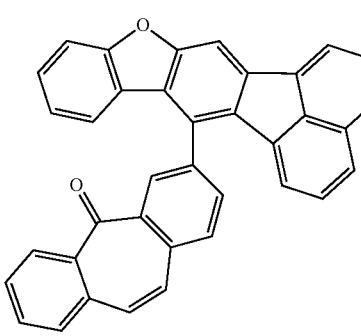

P71
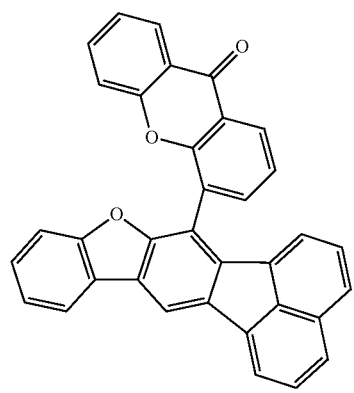
P72
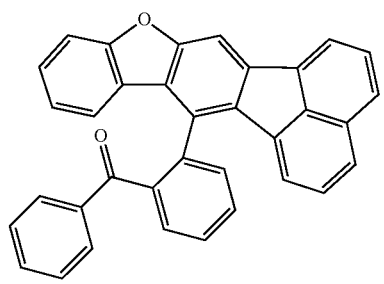
P73
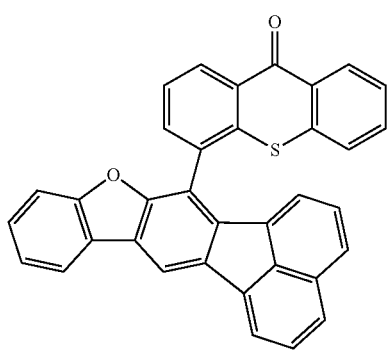
P74
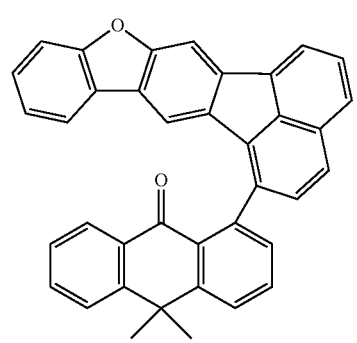
P75
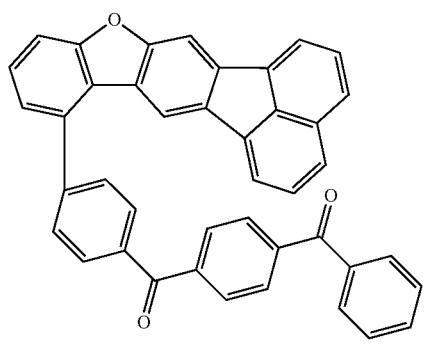
P76
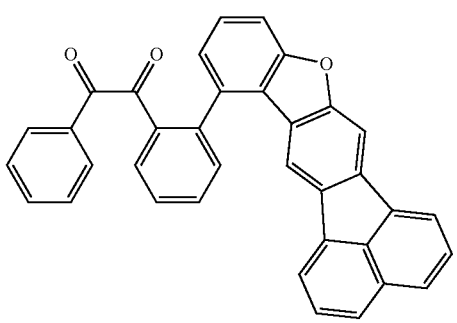
P77
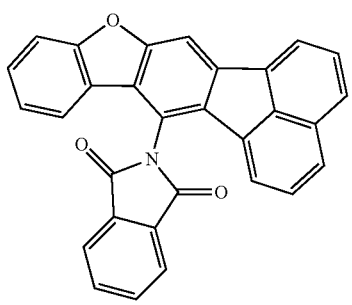
P78
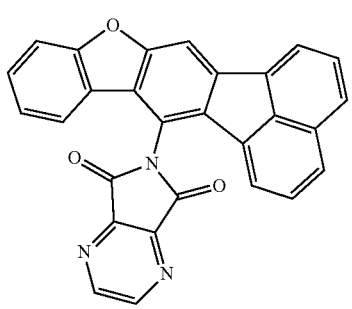

-continued
P79
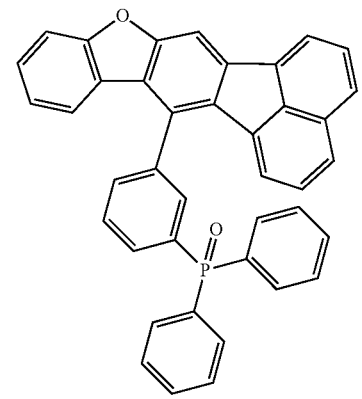
P80
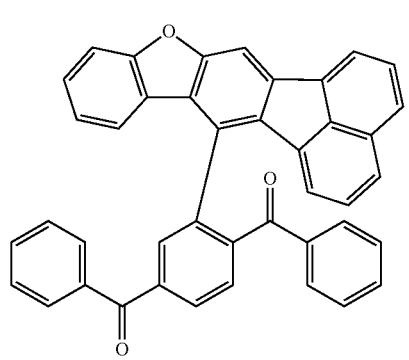
P81
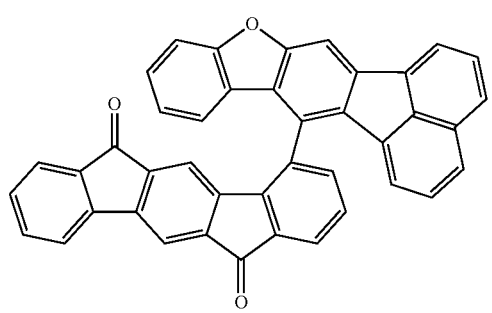
P82
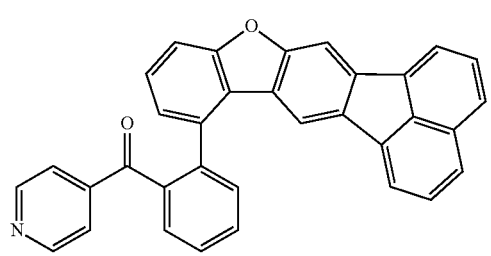
P83
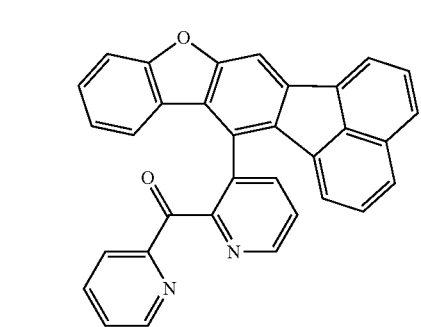
-continued
P84
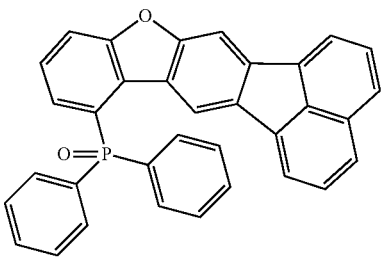
P85
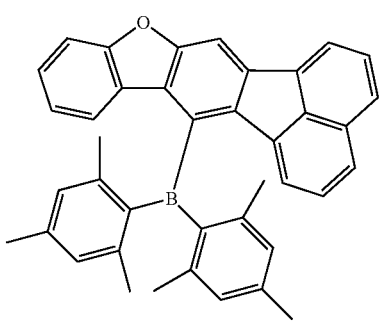
P86
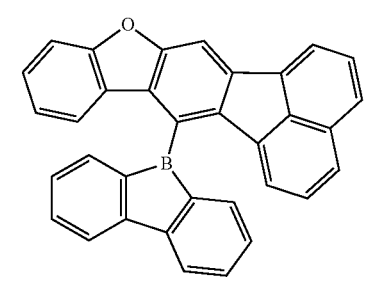
P87
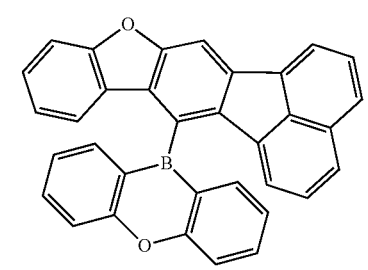
P88
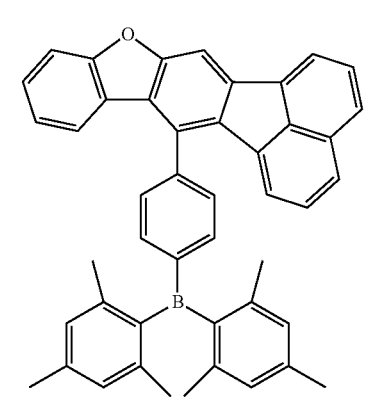

P89 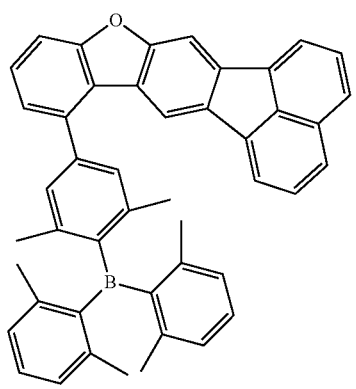
P90 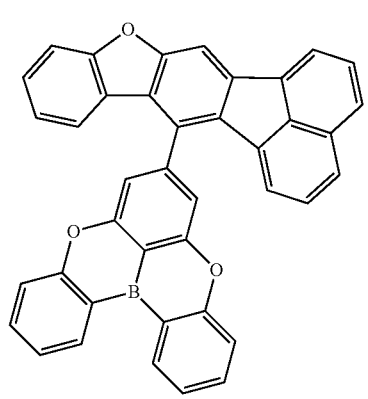
P91 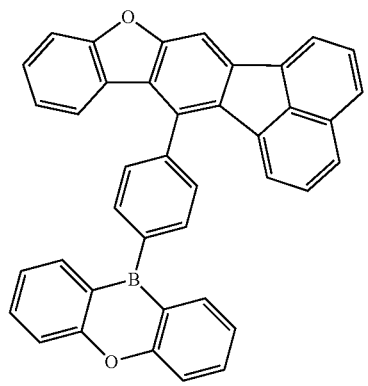
P92 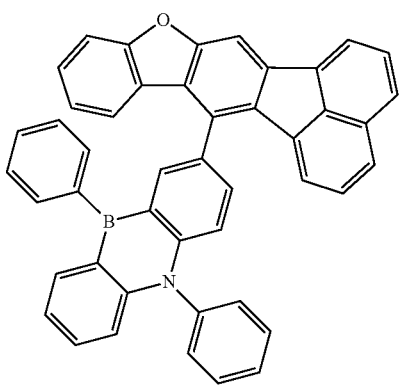
P93 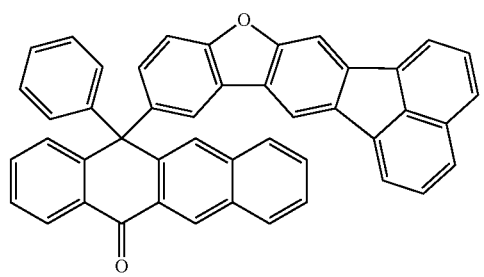
P94 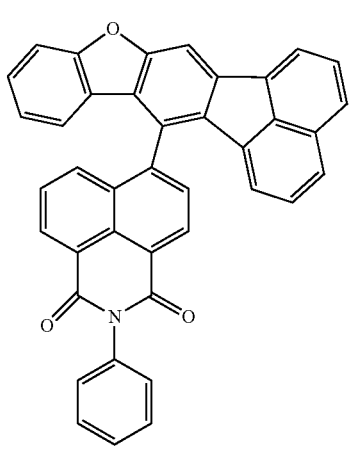
P95 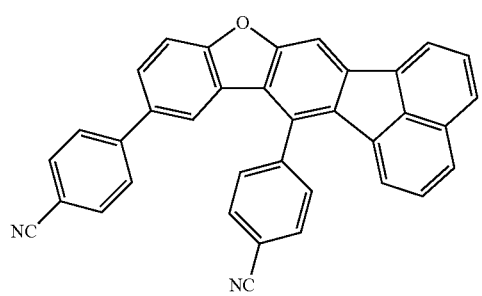
P96 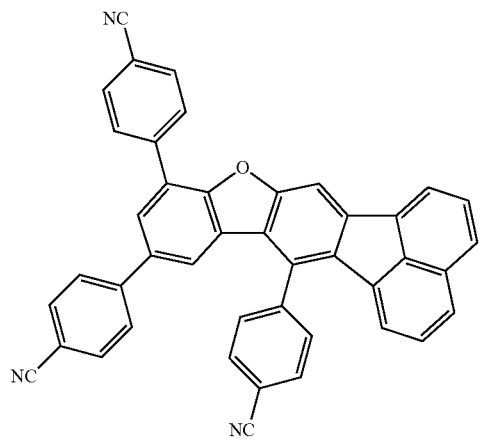

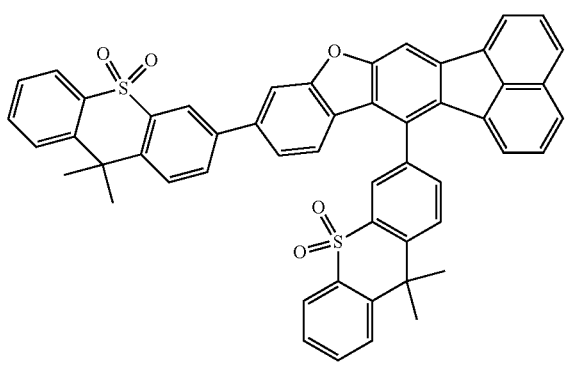

P97

In a second aspect, the present disclosure provides an organic electro-optical device. The organic electro-optical device comprises an anode, a cathode and at least one organic thin film layer located between the anode and the cathode.

The at least one organic thin film layer is one selected from the group consisting of a hole injection layer, a hole transport layer, an electron blocking layer, a light emitting layer, a hole blocking layer, an electron transport layer, an electron injection layer, and a combination of at least two selected therefrom, and comprises a light emitting layer.

At least one of the organic thin film layers comprises at least one of the compounds described in the first aspect.

The materials of the anode and the cathode are not particularly limited in the present disclosure. The anode material may be, for example, a metal such as copper, gold, silver, iron, chromium, nickel, manganese, palladium, platinum, etc., and an alloy thereof, a metal oxide such as indium oxide, zinc oxide, indium tin oxide (ITO), indium zinc oxide (IZO), etc., or a conductive polymer such as polyaniline, polypyrrole, poly(3-methylthiophene), etc. In addition to the above materials that facilitate hole injection and combinations thereof, the anode material may also be other known materials suitable for the anode. The cathode material may be a metal such as aluminum, magnesium, silver, indium, tin, titanium, etc., and an alloy thereof, or a multi-layer material such as LiF/Al, LiO$_2$/Al, BaF$_2$/Al, etc. In addition to the above materials that facilitate electron injection and combinations thereof, the cathode material may also be other known materials suitable for the cathode.

In one embodiment of the present disclosure, the organic electro-optical device comprises an anode, a hole injection layer, a hole transport layer, an electron blocking layer, a light emitting layer, a hole blocking layer, an electron transport layer, an electron injection layer and a cathode which are sequentially stacked.

In one embodiment of the present disclosure, a material of the electron transport layer is one selected from the group consisting of the compounds described in the first aspect, and a combination of at least two selected therefrom.

In one embodiment of the present disclosure, the electron transport layer comprises a host material and a guest material. The host material of the electron transport layer is one selected from the group consisting of the compounds described in the first aspect, and a combination of at least two selected therefrom.

In one embodiment of the present disclosure, a material of the hole blocking layer is one selected from the group consisting of the compounds described in the first aspect, and a combination of at least two selected therefrom. And the lowest triplet energy level of a light emitting material of the light emitting layer is lower than the lowest triplet energy level of the compound.

The following compounds and preparation methods thereof are provided exemplarily in examples of the present disclosure, and organic light emitting devices are prepared exemplarily by using the above compounds and preparation methods thereof.

Example 1

This example provides an organic compound. The structure of the organic compound is as follows:

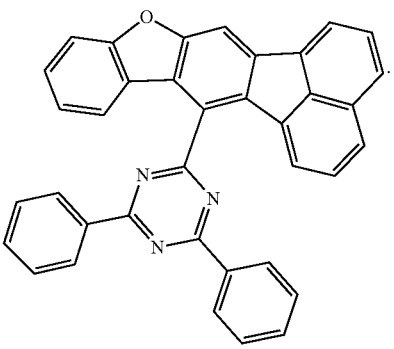

P1

The preparation method of the organic compound P1 includes the following steps.

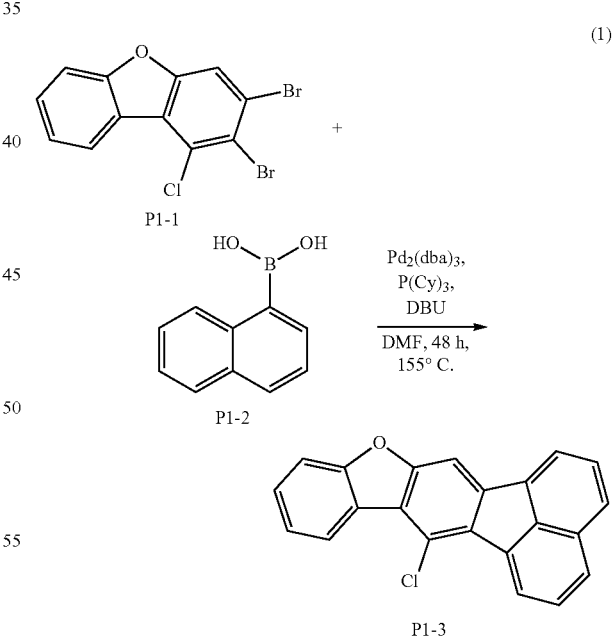

(1)

In a 100 mL round-bottomed flask, P1-1 (15 mmol), P1-2 (18 mmol), Pd$_2$(dba)$_3$ (0.20 mol), P (Cy)$_3$ (0.50 mol) and DBU (15 mL) were added to dried DMF (60 mL). The reaction was conducted for 48 h while stirring under nitrogen atmosphere with the temperature controlled at 155° C. The resulting intermediate was filtered through a pad of diatomite. The filtrate was extracted with dichloromethane, then washed twice with 50 mL of hydrochloric acid (10%), then washed once with 50 mL of water and dried over anhydrous magnesium sulfate. After filtration and evaporation, the organic phase was removed, and the solvent was removed by rotary evaporation. The resulting residue was subjected to silica gel column chromatography using a mixed solution including ethyl acetate and petroleum ether at a volume ratio of 1:2 as the eluent to give the solid product intermediate P1-3 (12.0 mmol, 80%).

ESI-MS (m/z) (M+) was obtained through liquid chromatography-mass spectrometry: the theoretical value is 326.1, and the test value is 326.5.

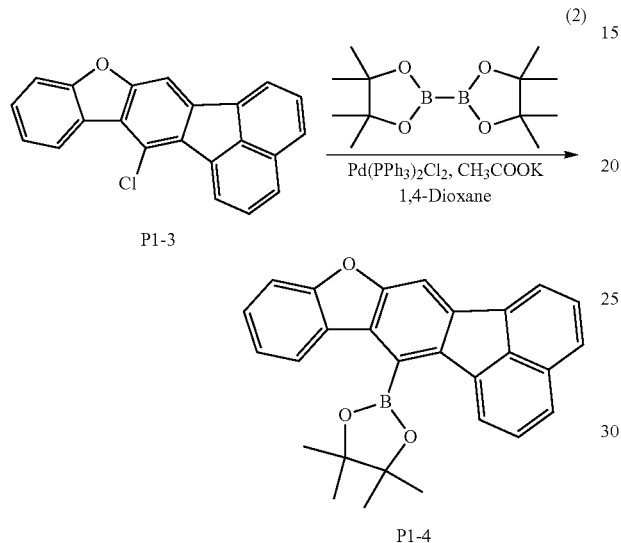

P1-3

P1-4

(2)

In a 100 mL round-bottomed flask, the intermediate P1-3 (15 mmol) and potassium acetate (40 mmol) were mixed with dried 1,4-dioxane (60 mL), Pd(PPh$_3$)$_2$C$_{12}$ (0.40 mmol) and bis(pinacolato)diboron (25 mmol), and the above mixture was stirred for 48 h at 90° C. under nitrogen atmosphere. The resulting intermediate was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the intermediate P1-4 (12.5 mmol, 83%).

ESI-MS (m/z) (M+) was obtained through liquid chromatography-mass spectrometry: the theoretical value is 418.2, and the test value is 418.6.

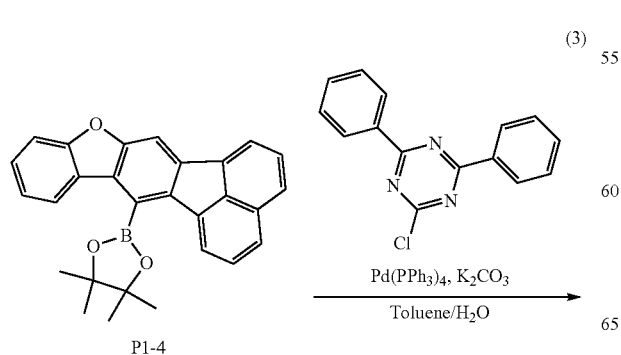

P1-4

(3)

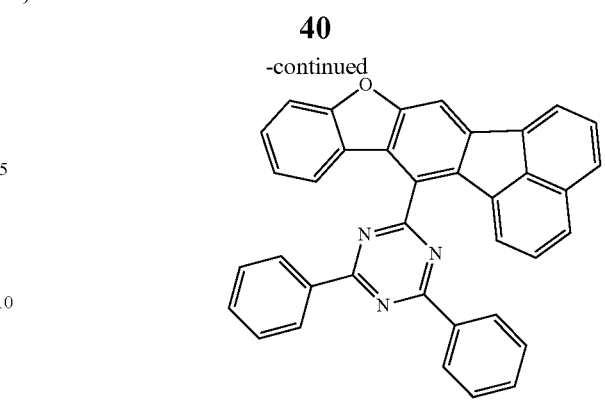

P1

In a 100 mL round-bottomed flask, P1-4 (10 mmol), 2-chloro-4,6-diphenyl-1,3,5-triazine (12 mmol) and Pd(PPh$_3$)$_4$ (0.3 mmol) were added in a mixture of methylbenzene (30 mL)/ethanol (20 mL) and an aqueous solution of potassium carbonate (12 mmol) (10 mL), and the reaction was refluxed for 12 h under nitrogen atmosphere. The resulting mixture was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P1 (7.8 mmol, 78%).

The characterization results of the organic compound P1 are as follows.

$^1$H-NMR (400 MHz, CDCl$_3$): δ 7.90 (d, J=5.6 Hz, 2H), 7.79-7.58 (m, 4H), 7.50-7.48 (m, 5H), 7.42 (d, J=2.4 Hz, 1H), 7.38 (s, 1H), 7.32-7.22 (m, 6H), 7.19-7.13 (m, 2H)

The elemental analysis results are: C$_{37}$H$_{21}$N$_3$O, theoretical values: C, 84.88, H, 4.04, N, 8.03, O, 3.06, test values: C, 84.84, H, 4.02, N, 8.05, O, 3.09.

ESI-MS (m/z) (M+) was obtained through liquid chromatography-mass spectrometry: the theoretical value is 523.2, and the test value is 523.5.

Example 2

This example provides an organic compound. The structure of the organic compound is as follows:

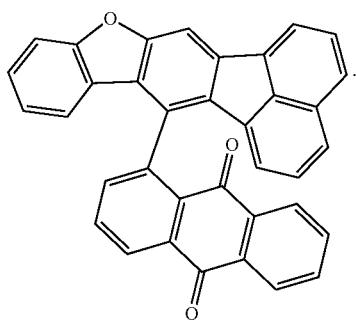

P7

The preparation method of the organic compound P7 includes the following steps.

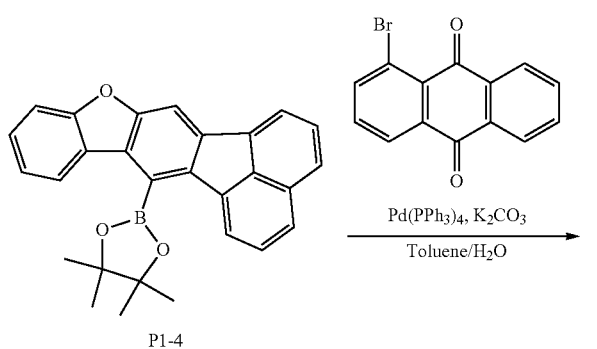

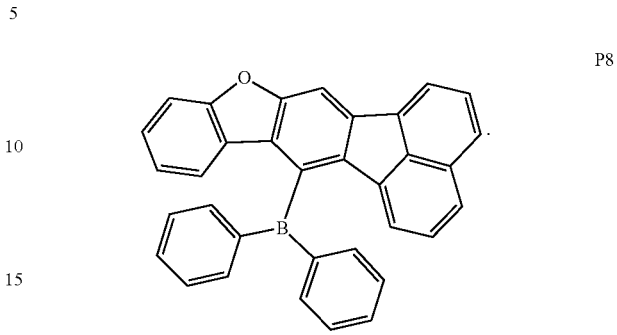

Example 3

This example provides an organic compound. The structure of the organic compound is as follows:

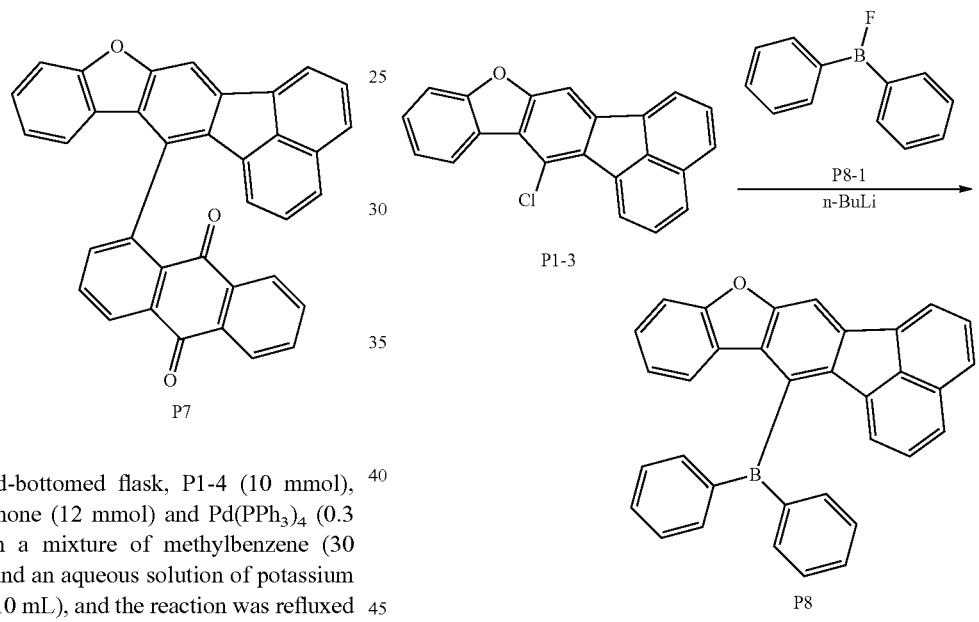

The preparation method of the organic compound P8 includes the following steps.

In a 100 mL round-bottomed flask, P1-4 (10 mmol), 2-bromo-1,4-benzoquinone (12 mmol) and Pd(PPh$_3$)$_4$ (0.3 mmol) were added in a mixture of methylbenzene (30 mL)/ethanol (20 mL) and an aqueous solution of potassium carbonate (12 mmol) (10 mL), and the reaction was refluxed for 12 h under nitrogen atmosphere. The resulting mixture was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P7 (6.2 mmol, 62%).

The characterization results of the organic compound P7 are as follows.

$^1$H-NMR (400 MHz, CDCl$_3$): δ 7.94 (d, J=5.6 Hz, 2H), 7.80-7.58 (m, 9H), 7.55 (d, J=3.4 Hz, 2H), 7.49-7.42 (m, 2H), 7.39 (s, 1H), 7.19-7.13 (m, 2H)

The elemental analysis results are: C$_{36}$H$_{18}$O$_3$, theoretical values: C, 86.73, H, 3.64, O 9.63, test values: C, 86.70, H, 3.65, O, 9.65.

ESI-MS (m/z) (M+) was obtained through liquid chromatography-mass spectrometry: the theoretical value is 498.1, and the test value is 498.3.

In a 100 mL round-bottomed flask, P1-3 (10 mmol) was dissolved in THF (40 mL). Under nitrogen atmosphere with the temperature controlled at −78° C., n-butyllithium (12 mmol) was slowly dropped thereinto. The reaction was conducted for 2 h at this temperature. P8-1 (12 mmol) was dropped and dissolved in THF (10 mL) and reacted for 6 h. The resulting mixture was added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P8 (6.5 mmol, 65%).

The characterization results of the organic compound P8 are as follows.

$^1$H-NMR (400 MHz, CDCl$_3$): δ 7.92 (d, J=5.3 Hz, 2H), 7.79-7.58 (m, 4H), 7.51-7.46 (m, 2H), 7.43 (s, 1H), 7.41-7.38 (m, 10H), 7.19-7.13 (m, 2H)

The elemental analysis results are: C$_{34}$H$_{21}$BO, theoretical values: C, 89.49, H, 4.64, B, 2.37, O, 3.51, test values: C, 89.46, H, 4.65, B, 2.38, O, 3.51.

ESI-MS (m/z) (M+) was obtained through liquid chromatography-mass spectrometry: the theoretical value is 456.2, and the test value is 456.6.

Example 4

This example provides an organic compound. The structure of the organic compound is as follows:

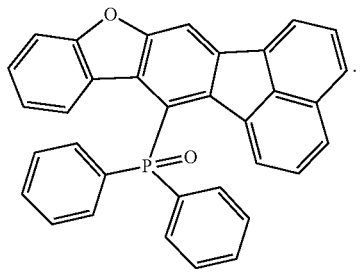

P24

The preparation method of the organic compound P24 includes the following steps.

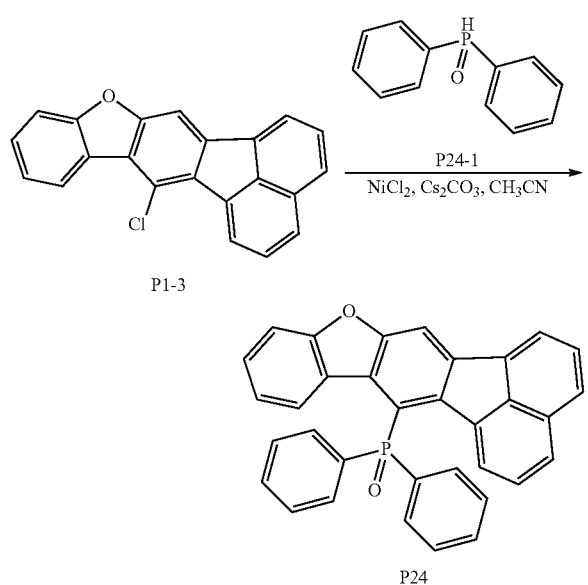

In a 100 mL round-bottomed flask, P1-3 (10 mmol), P24-1 (12 mmol), 10% NiCl$_2$ and Cs$_2$CO$_3$ (10 mmol) were added to acetonitrile (50 mL) and reacted under microwave irradiation at 155° C. for 12 h under nitrogen atmosphere. The resulting mixture was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P24 (7.5 mmol, 75%).

The characterization results of the organic compound P24 are as follows.

$^1$H-NMR (400 MHz, CDCl$_3$): δ 7.96 (d, J=4.3 Hz, 2H), 7.79-7.58 (m, 4H), 7.56-7.49 (m, 10H), 7.48-7.43 (m, 2H), 7.42 (s, 1H), 7.20-7.12 (m, 2H)

The elemental analysis results are: C$_{34}$H$_{21}$O$_2$P, theoretical values: C, 82.91, H, 4.30, O, 6.50, P, 6.29, test values: C, 82.90, H, 4.31, O, 6.51, P, 6.29.

ESI-MS (m/z) (M+) was obtained through liquid chromatography-mass spectrometry: the theoretical value is 492.1, and the test value is 492.0.

Example 5

This example provides an organic compound. The structure of the organic compound is as follows:

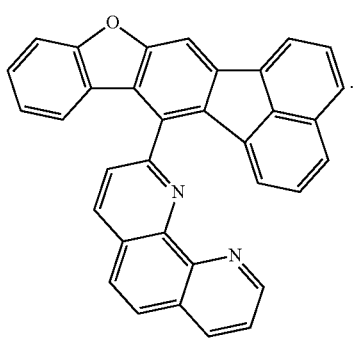

P45

The preparation method of the organic compound P45 includes the following steps.

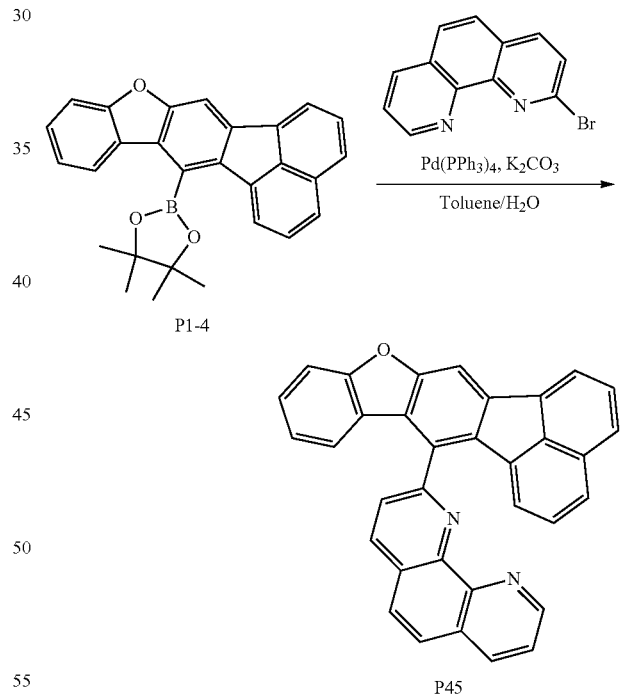

In a 100 mL round-bottomed flask, P1-4 (10 mmol), 2-bromo-o-phenanthroline (12 mmol) and Pd(PPh$_3$)$_4$ (0.3 mmol) were added in a mixture of methylbenzene (30 mL)/ethanol (20 mL) and an aqueous solution of potassium carbonate (12 mmol) (10 mL), and the reaction was refluxed for 12 h under nitrogen atmosphere. The resulting mixture was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P45 (6.7 mmol, 67%).

The characterization results of the organic compound P45 is as follows.

$^1$H-NMR (400 MHz, CDCl$_3$): δ 9.61 (d, J=2.6 Hz, 1H), 9.01-8.86 (m, 1H), 8.63 (d, J=2.3 Hz, 1H), 7.90 (d, J=1.6 Hz, 1H), 7.79-7.58 (m, 6H), 7.49-7.26 (m, 5H), 7.44 (s, 1H), 7.19-7.13 (m, 2H)

The elemental analysis results are: C$_{34}$H$_{18}$N$_2$O, theoretical values: C, 86.79, H, 3.86, N, 5.95, O, 3.40, test values: C, 86.76, H, 3.87, N, 5.96, O, 3.41.

ESI-MS (m/z) (M+) was obtained through liquid chromatography-mass spectrometry: the theoretical value is 470.1, and the test value is 470.5.

Example 6

This example provides an organic compound. The structure of the organic compound is as follows:

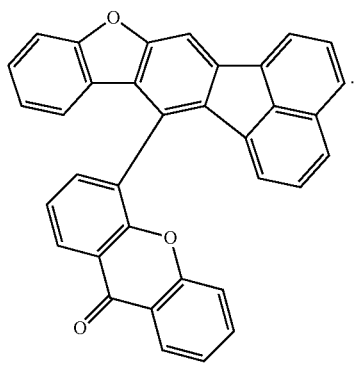

P69

The preparation method of the organic compound P69 includes the following steps.

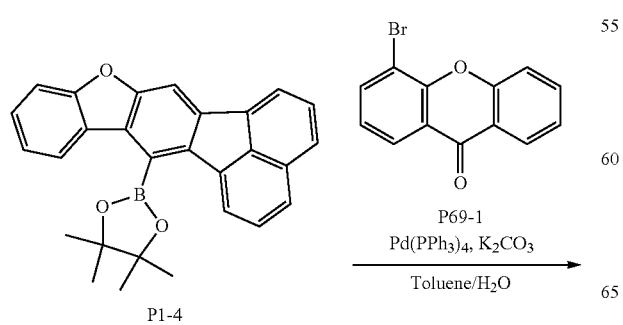

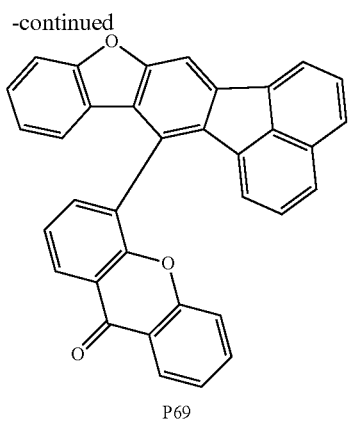

P69

In a 100 mL round-bottomed flask, P1-4 (10 mmol), P69-1 (12 mmol) and Pd(PPh$_3$)$_4$ (0.3 mmol) were added in a mixture of methylbenzene (30 mL)/ethanol (20 mL) and an aqueous solution of potassium carbonate (12 mmol) (10 mL), and the reaction was refluxed for 12 h under nitrogen atmosphere. The resulting mixture was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P69 (5.7 mmol, 57%).

The characterization results of the organic compound P69 is as follows.

$^1$H-NMR (400 MHz, CDCl$_3$): δ 7.91 (d, J=5.9 Hz, 2H), 7.81-7.58 (m, 9H), 7.52 (d, J=3.4 Hz, 2H), 7.50-7.42 (m, 2H), 7.37 (s, 1H), 7.19-7.12 (m, 2H)

The elemental analysis results are: C$_{35}$H$_{18}$O$_3$, theoretical values: C, 86.40, H, 3.73, O, 9.87, test values: C, 86.41, H, 3.72, O, 9.87.

ESI-MS (m/z) (M+) was obtained through liquid chromatography-mass spectrometry: the theoretical value is 486.1, and the test value is 486.5.

Example 7

This example provides an organic compound. The structure of the organic compound is as follows:

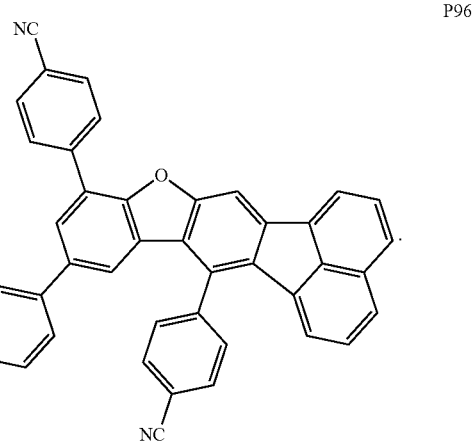

P96

The preparation method of the organic compound P96 includes the following steps.

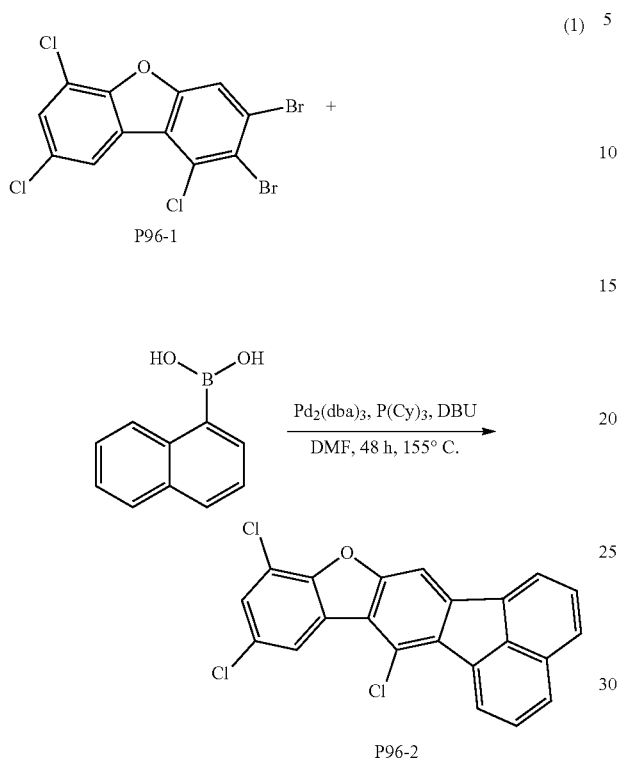

(1)

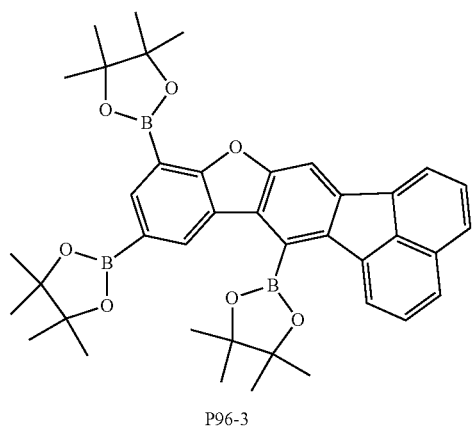

In a 100 mL round-bottomed flask, P96-1 (15 mmol), 1-naphthaleneboronic acid (18 mmol), Pd$_2$(dba)$_3$ (0.20 mol), P(Cy)$_3$ (0.50 mol) and DBU (15 mL) were added to dried DMF (60 mL). The reaction was conducted for 48 h while stirring under nitrogen atmosphere with the temperature controlled at 155° C. The resulting intermediate was filtered through a pad of diatomite. The filtrate was extracted with dichloromethane, then washed twice with 50 mL of hydrochloric acid (10%), then washed once with 50 mL of water and dried over anhydrous magnesium sulfate. After filtration and evaporation, the organic phase was removed, and the solvent was removed by rotary evaporation. The resulting residue was subjected to silica gel column chromatography using a mixed solution including ethyl acetate and petroleum ether at a volume ratio of 1:2 as the eluent to give the solid product intermediate P96-2 (8.7 mmol, 58%).

ESI-MS (m/z) (M+) was obtained through liquid chromatography-mass spectrometry: the theoretical value is 394.0, and the test value is 394.2.

In a 100 mL round-bottomed flask, the intermediate P96-2 (15 mmol) and potassium acetate (40 mmol) were mixed with dried 1,4-dioxane (60 mL), Pd(PPh$_3$)$_2$C$_{12}$ (0.40 mmol) and bis(pinacolato)diboron (60 mmol), and the above mixture was stirred for 48 h at 90° C. under nitrogen atmosphere. The resulting intermediate was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the intermediate P96-3 (11.0 mmol, 73%).

ESI-MS (m/z) (M+) was obtained through liquid chromatography-mass spectrometry: the theoretical value is 670.3, and the test value is 670.8.

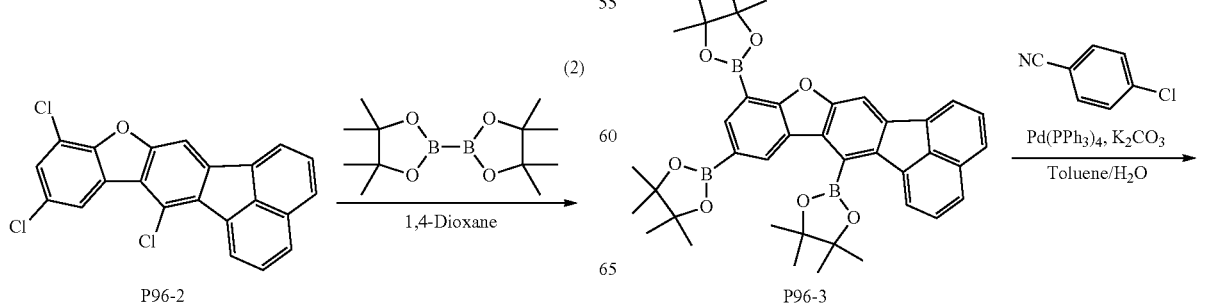

(3)

-continued

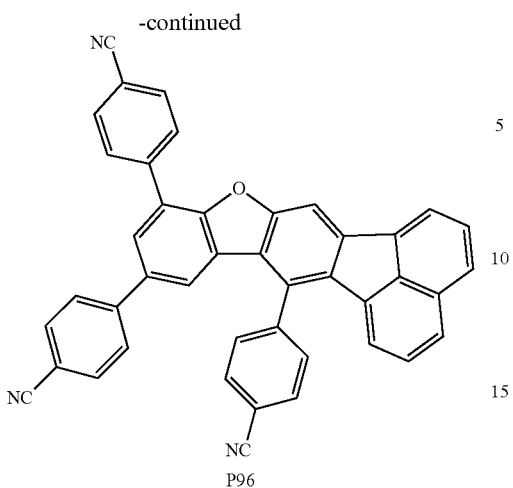

P96

In a 100 mL round-bottomed flask, P96-3 (10 mmol), 4-cyanochlorobenzene (35 mmol) and Pd(PPh$_3$)$_4$ (0.5 mmol) were added in a mixture of methylbenzene (30 mL)/ethanol (20 mL) and an aqueous solution of potassium carbonate (12 mmol) (10 mL), and the reaction was refluxed for 12 h under nitrogen atmosphere. The resulting mixture was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P96 (6.3 mmol, 63%).

The characterization results of the organic compound P96 is as follows.

$^1$H-NMR (400 MHz, CDCl$_3$): δ 7.90-7.79 (m, 4H), 7.67 (s, 1H), 7.66-7.63 (m, 14H), 7.57 (s, 1H), 7.38 (s, 1H)

The elemental analysis results are: C$_{43}$H$_{21}$N$_3$O, theoretical values: C, 86.71, H, 3.55, N, 7.05, O, 2.69, test values: C, 86.70, H, 3.56, N, 7.04, O, 2.70.

ESI-MS (m/z) (M+) was obtained through liquid chromatography-mass spectrometry: the theoretical value is 595.2, and the test value is 595.2.

Example 8

This example provides an organic compound. The structure of the organic compound is as follows:

P97

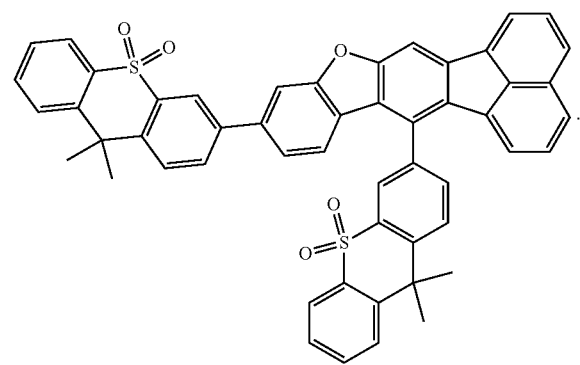

The preparation method of the organic compound P97 includes the following steps.

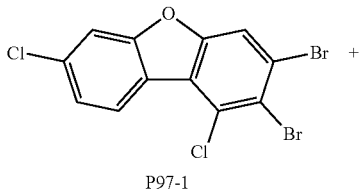

P97-1

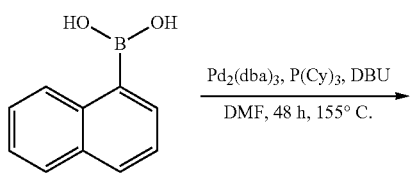

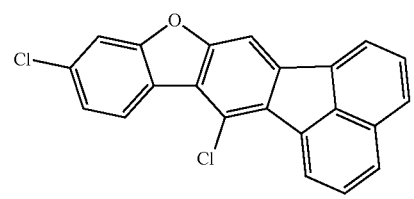

P97-2

In a 100 mL round-bottomed flask, P97-1 (15 mmol), 1-naphthaleneboronic acid (18 mmol), Pd$_2$(dba)$_3$ (0.20 mol), P(Cy)$_3$ (0.50 mol) and DBU (15 mL) were added to dried DMF (60 mL). The reaction was conducted for 48 h while stirring under nitrogen atmosphere with the temperature controlled at 155° C. The resulting intermediate was filtered through a pad of diatomite. The filtrate was extracted with dichloromethane, then washed twice with 50 mL of hydrochloric acid (10%), then washed once with 50 mL of water and dried over anhydrous magnesium sulfate. After filtration and evaporation, the organic phase was removed, and the solvent was removed by rotary evaporation. The resulting residue was subjected to silica gel column chromatography using a mixed solution including ethyl acetate and petroleum ether at a volume ratio of 1:2 as the eluent to give the solid product intermediate P97-2 (10.4 mmol, 69%).

ESI-MS (m/z) (M+) was obtained through liquid chromatography-mass spectrometry: the theoretical value is 360.0, and the test value is 360.2.

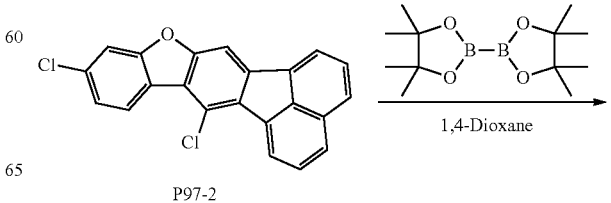

P97-2

-continued

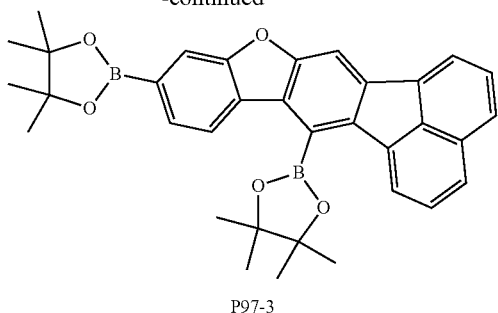

P97-3

In a 100 mL round-bottomed flask, the intermediate P97-2 (15 mmol) and potassium acetate (40 mmol) were mixed with dried 1,4-dioxane (60 mL), Pd(PPh$_3$)$_2$C$_{12}$ (0.40 mmol) and bis(pinacolato)diboron (30 mmol), and the above mixture was stirred for 48 h at 90° C. under nitrogen atmosphere. The resulting intermediate was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the intermediate P97-3 (10.7 mmol, 71%).

ESI-MS (m/z) (M+) was obtained through liquid chromatography-mass spectrometry: the theoretical value is 544.3, and the test value is 544.5.

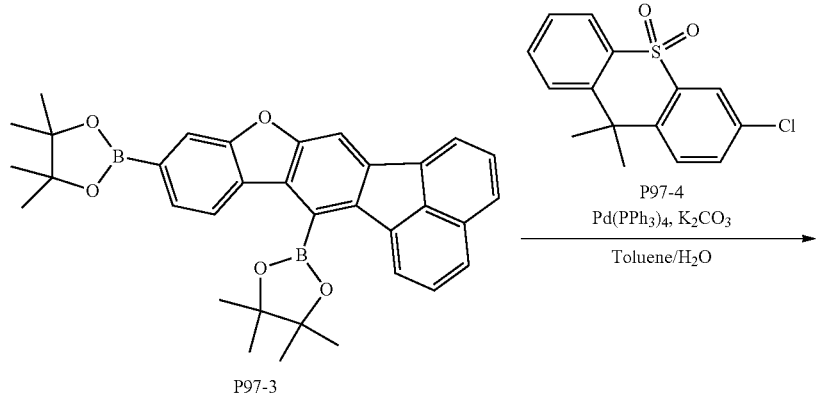

(3)

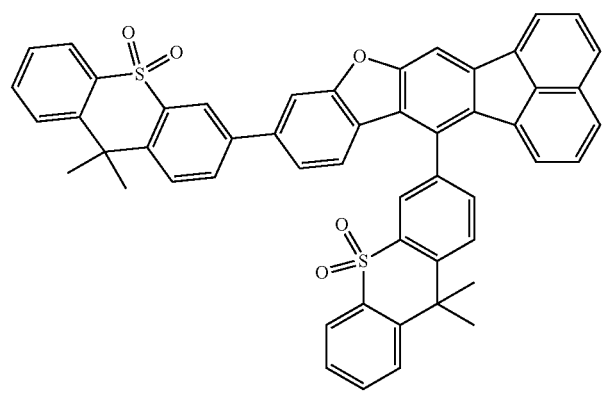

P97

In a 100 mL round-bottomed flask, P97-3 (10 mmol), P97-4 (25 mmol) and Pd(PPh$_3$)$_4$ (0.4 mmol) were added in a mixture of methylbenzene (30 mL)/ethanol (20 mL) and an aqueous solution of potassium carbonate (12 mmol) (10 mL), and the reaction was refluxed for 12 h under nitrogen atmosphere. The resulting mixture was cooled to room temperature, added to water and then filtered through a pad of diatomite. The filtrate was extracted with dichloromethane, then washed with water and dried over anhydrous magnesium sulfate. After filtration and evaporation, the crude product was purified through silica gel column chromatography to give the final product P97 (4.6 mmol, 46%).

The characterization results of the organic compound P97 are as follows.

$^1$H-NMR (400 MHz, CDCl$_3$): δ 8.14 (d, J=1.6 Hz, 2H), 7.90-7.79 (m, 6H), 7.64 (s, 1H), 7.58-7.40 (m, 5H), 7.39 (s, 1H), 7.36-7.20 (m, 9H), 1.92 (s, 12H)

The elemental analysis results are: C$_{52}$H$_{36}$O$_5$S$_2$, theoretical values: C, 77.59, H, 4.51, O, 9.94, S, 7.97, test values: C, 77.57, H, 4.53, O, 9.94, S, 7.96.

ESI-MS (m/z) (M+) was obtained through liquid chromatography-mass spectrometry: the theoretical value is 804.2, and the test value is 804.5.

Simulating Calculation of Compound Energy Level

With the application of the density functional theory (DFT), for the organic compounds provided by the examples of the present disclosure as well as compound 1

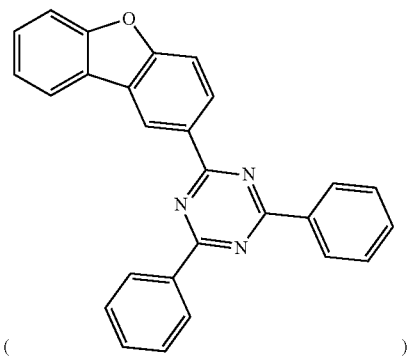 [SMILES: c1ccc(-c2nc(-c3ccccc3)nc(-c3ccc4oc5ccccc5c4c3)n2)cc1]

( )

and compound 2

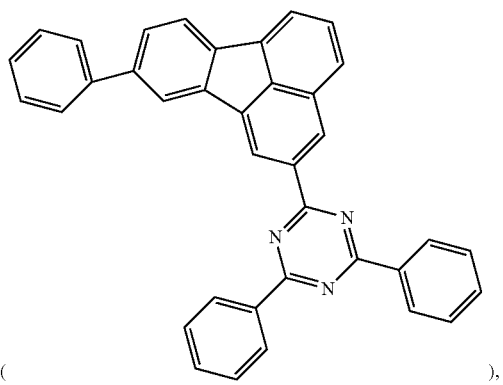 [SMILES: c1ccc(-c2ccc3c(c2)-c2cc(-c4nc(-c5ccccc5)nc(-c5ccccc5)n4)cc4cccc-3c24)cc1]

( ), the distributions of HOMO and LUMO of molecular frontier orbitals were optimized and calculated by using Guassian 09 program package (Guassian Inc.) at the calculation level of B3LYP/6-31G (d). Meanwhile, the lowest singlet energy level S$_1$ and the lowest triplet energy level T$_1$ of the compound molecules were simulated and calculated based on time-dependent density functional theory (TDDFT). The results are shown in Table 1.

TABLE 1

Compound Energy Level Data

| Compound | HOMO (eV) | LUMO (eV) | $E_{S1}$ (eV) | $E_{T1}$ (eV) |
|---|---|---|---|---|
| P1  | −5.60 | −1.94 | 3.15 | 2.33 |
| P7  | −5.50 | −2.83 | 2.13 | 2.03 |
| P8  | −5.47 | −1.85 | 2.99 | 2.32 |
| P24 | −5.63 | −1.74 | 3.33 | 2.35 |
| P45 | −5.28 | −1.81 | 2.98 | 2.19 |
| P69 | −5.66 | −1.85 | 3.20 | 2.33 |
| P86 | −5.50 | −1.89 | 3.01 | 2.13 |
| P96 | −5.61 | −1.83 | 3.02 | 2.24 |
| P97 | −5.86 | −1.99 | 2.99 | 2.32 |
| Compound 1 | −6.13 | −1.61 | 3.80 | 2.98 |
| Compound 2 | −5.69 | −2.12 | 3.06 | 1.95 |

As can be seen from Table 1, the compound provided by the present disclosure has a deeper LUMO energy level (absolute value <−1.7 eV) and a higher lowest triplet energy level $E_{T1}$ (>2.0 eV), which is beneficial to electron injection and blocking of light-emitting layer excitons. The compound is suitable to be used as the electron transport material, improving the electron mobility and luminescence efficiency of the organic light-emitting device.

Application Example 1

This application example provides an OLED device. The OLED device includes a substrate, an anode (ITO), a hole injection layer, a first hole transport layer, a second hole transport layer, a light emitting layer, an electron transport layer, an electron injection layer, a cathode (magnesium-silver electrode with magnesium and silver at a mass ratio of 9:1) and a capping layer (CPL) which are sequentially stacked.

The thickness of the ITO anode is 15 nm, the thickness of the hole injection layer is 5 nm, the thickness of the first hole transport layer is 100 nm, the thickness of the second hole transport layer is 5 nm, the thickness of the light emitting layer is 30 nm, the thickness of the electron transport layer is 30 nm, the thickness of the electron injection layer is 5 nm, the thickness of magnesium-silver cathode is 10 nm, and the thickness of the CPL is 100 nm.

The specific preparation steps of the above OLED device are as follows.

1) A glass substrate with an ITO anode (with a thickness of 15 nm) was cut into a size of 50 mm×50 mm×0.7 mm, and sonicated in isopropanol and deionized water for 30 minutes, respectively, then exposed to ozone for about 10 minutes for cleaning, and the cleaned glass substrate was mounted on a vacuum deposition device.

2) A hole injection layer material compound b and a p-type doping material compound a were evaporated together on the ITO anode layer in a vacuum evaporation mode as the hole injection layer, where the doping proportion is 3% (mass ratio), and the thickness is 5 nm.

3) A hole transport material compound c was evaporated in vacuum on the hole injection layer with a thickness of 100 nm as the first hole transport layer.

4) A hole transport material compound d was evaporated in vacuum on the first hole transport layer with a thickness of 5 nm as the second hole transport layer.

5) A light emitting layer host material compound e and a doping material compound f were evaporated in vacuum together on the second hole transport layer as the light emitting layer, where the doping proportion is 3% (mass ratio), and the thickness is 30 nm.

6) A compound P1 was evaporated in vacuum on the light emitting layer with a thickness of 30 nm as the electron transport layer.

7) A compound g and a n-type doping material compound h were evaporated in vacuum together on the electron transport layer as the electron injection layer, where the doping mass ratio is 1:1, and the thickness is 5 nm.

8) A magnesium-silver electrode was evaporated in vacuum on the electron injection layer as the cathode, where the mass ratio of Mg:Ag is 1:9, and the thickness is 10 nm.

9) a compound i was evaporated in vacuum on the cathode with a thickness of 100 nm as the CPL.

The compounds used in the preparation process of the OLED device are as follows.

Compound a

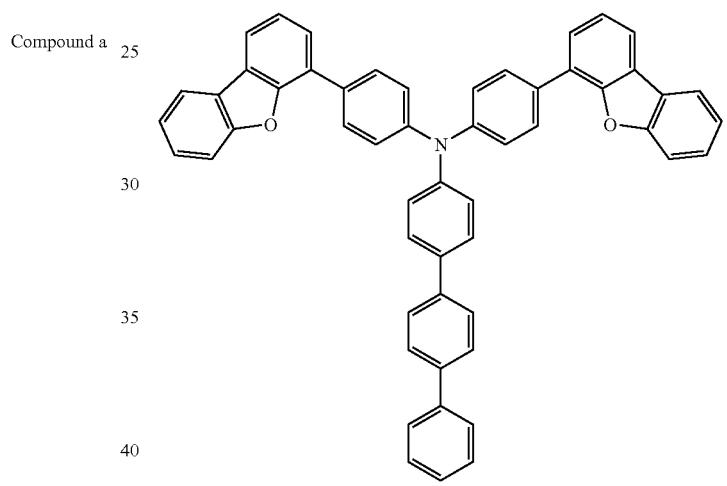

Compound b

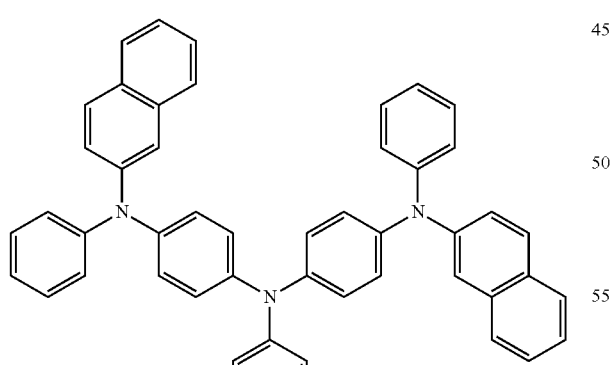

Compound c

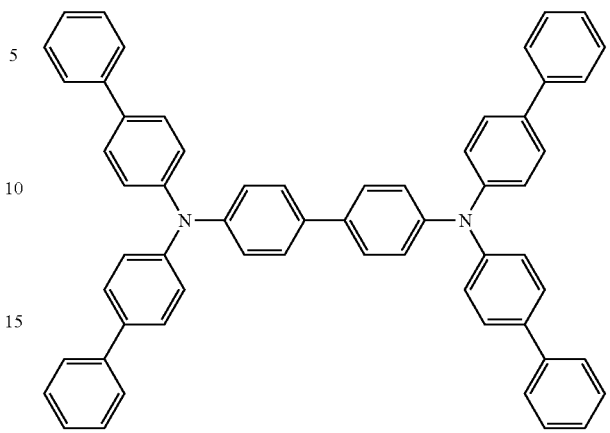

Compound d

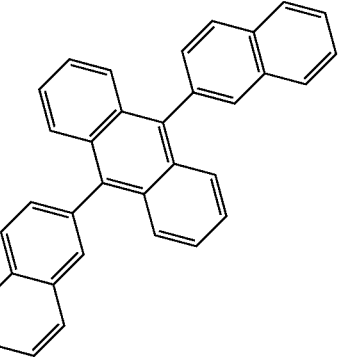

Compound e

Compound f

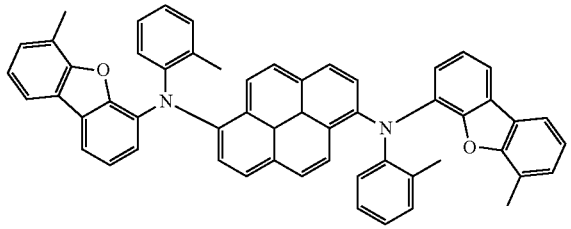

Compound g

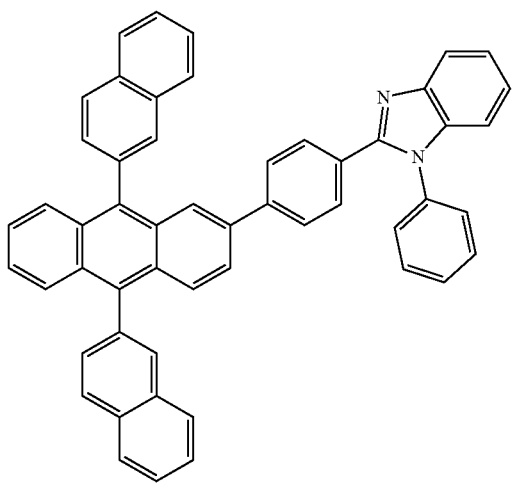

Compound h

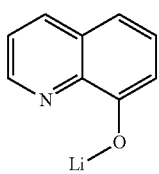

Compound i

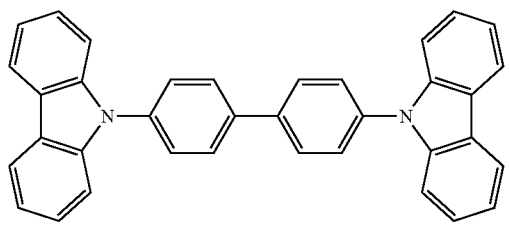

Application Example 2

This application example differs from the application example 1 only in that the organic compound P1 in step (6) is replaced with the organic compound P7, and other preparation steps are the same.

Application Example 3

This application example differs from the application example 1 only in that the organic compound P1 in step (6) is replaced with the organic compound P8, and other preparation steps are the same.

Application Example 4

This application example differs from the application example 1 only in that the organic compound P1 in step (6) is replaced with the organic compound P24, and other preparation steps are the same.

Application Example 5

This application example differs from the application example 1 only in that the organic compound P1 in step (6) is replaced with the organic compound P45, and other preparation steps are the same.

Application Example 6

This application example differs from the application example 1 only in that the organic compound P1 in step (6) is replaced with the organic compound P69, and other preparation steps are the same.

Application Example 7

This application example differs from the application example 1 only in that the organic compound P1 in step (6) is replaced with the organic compound P86, and other preparation steps are the same.

Application Example 8

This application example differs from the application example 1 only in that the organic compound P1 in step (6) is replaced with the organic compound P96, and other preparation steps are the same.

Application Example 9

This application example differs from the application example 1 only in that the organic compound P1 in step (6) is replaced with the organic compound P97, and other preparation steps are the same.

Comparison Example 1

This comparison example differs from the application example 1 only in that the organic compound P1 in step (6) is replaced with a comparison compound 1

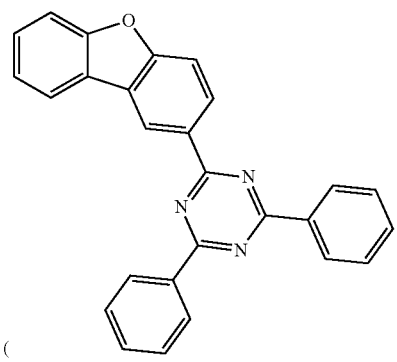

( ), and other preparation steps are the same.

Comparison Example 2

This comparison example differs from the application example 1 only in that the organic compound P1 in step (6) is replaced with a comparison compound 2

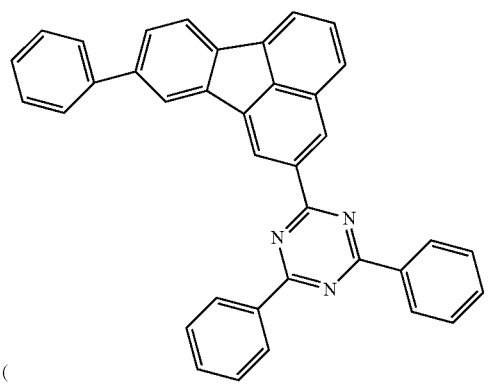

and other preparation steps are the same.

Performance Evaluation of the OLED Device

The currents of the OLED device under different voltages were tested by using the Keithley 2365A digital nanovolt meter. The current densities of the OLED device under different voltages were obtained by dividing each current by the light-emitting area. The brightness and radiant energy flux densities of the OLED device under different voltages were tested by using the Konicaminolta CS-2000 spectroradiometer. The working voltage and current efficiency (cd/A) under the same current density (10 mA/cm$^2$) were obtained according to the current densities and the brightnesses of the OLED device under different voltages, and $V_{on}$ is the turn-on voltage under the brightness of 1 cd/m$^2$. The lifetime LT95 was obtained by measuring the time at which the brightness of the OLED device reached 95% of the initial brightness (under the test condition of 50 mA/cm$^2$). The test data are shown in Table 2.

TABLE 2

| OLED device | Electrode transport layer material | $V_{on}$ (V) | Current efficiency (cd/A) | Service life LT95 (h) |
|---|---|---|---|---|
| Application example 1 | P1 | 3.69 | 5.6 | 73 |
| Application example 2 | P7 | 3.97 | 5.8 | 66 |
| Application example 3 | P8 | 3.83 | 5.3 | 67 |
| Application example 4 | P24 | 4.00 | 4.8 | 68 |
| Application example 5 | P45 | 3.74 | 5.6 | 70 |
| Application example 6 | P69 | 3.68 | 4.9 | 65 |
| Application example 7 | P86 | 3.78 | 5.8 | 54 |
| Application example 8 | P96 | 3.84 | 5.1 | 66 |
| Application example 9 | P97 | 3.67 | 5.4 | 53 |
| Comparison example 1 | Compound 1 | 4.21 | 3.5 | 45 |
| Comparison example 2 | Compound 2 | 4.43 | 4.1 | 46 |

As can be seen from Table 1 and Table 2, compared with compounds 1 and 2, since the compound provided by the present disclosure has stronger rigidity and a more stable molecular structure, the compound is more beneficial to film formation in vacuum deposition mode, and the stability of the thin film of the electron transport layer is more stable. Therefore, the service life of the prepared OLED device is longer. In addition, since the compound provided by the present disclosure has a deeper LUMO energy level and a larger conjugated structure, the compound is beneficial to electron injection and transport. Therefore, the prepared OLED device has a lower turn-on voltage and a higher current efficiency.

What is claimed is:

1. A compound having a structure represented by Formula II:

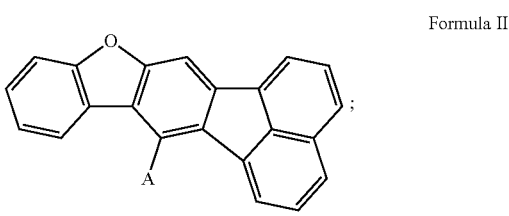

Formula II wherein A is any one selected from the group consisting of a cyano-containing electron acceptor group, a nitrogen heterocycle-containing electron acceptor group, a sulfone-containing electron acceptor group, a carbonyl-containing electron acceptor group, a phosphinyloxy-containing electron acceptor group and a boron-containing electron acceptor group.

2. The compound according to claim 1, wherein the cyano-containing electron acceptor group is any one selected from the group consisting of the following groups:

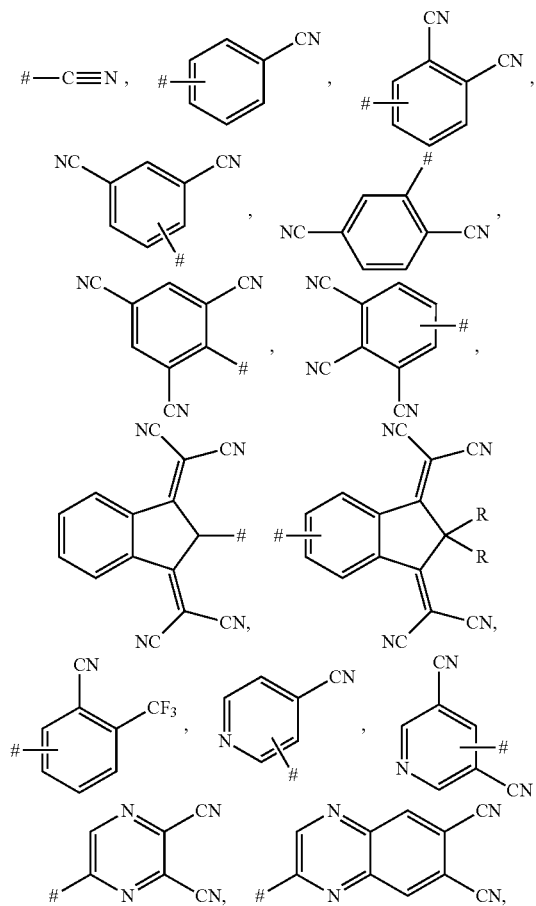

61
-continued

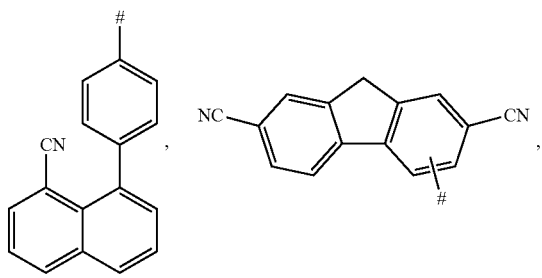

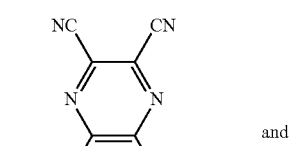

and

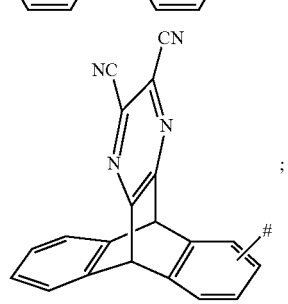

;

wherein R is any one selected from the group consisting of a hydrogen atom, $C_1$-$C_{20}$ alkyl, $C_1$-$C_{20}$ alkoxy, $C_6$-$C_{30}$ aryl and $C_2$-$C_{30}$ heteroaryl, and #represents a linkage position of groups.

3. The compound according to claim 1, wherein the nitrogen heterocycle-containing electron acceptor group is any one selected from the group consisting of the following groups:

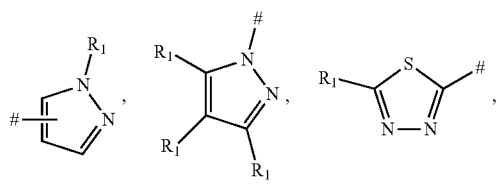

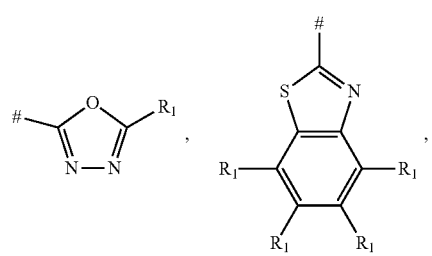

62
-continued

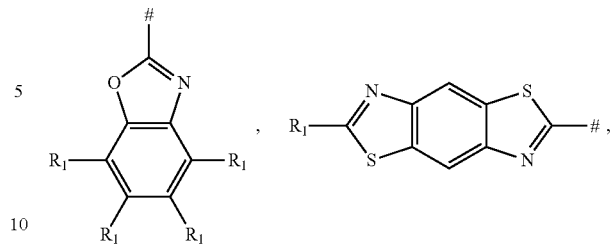

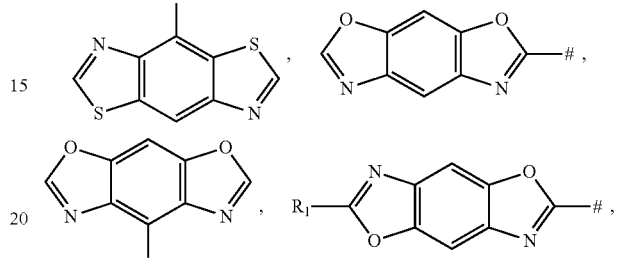

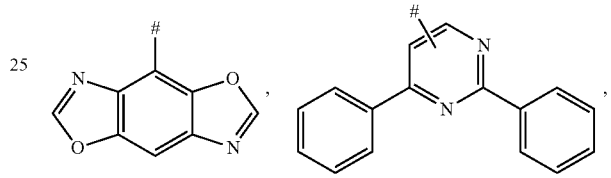

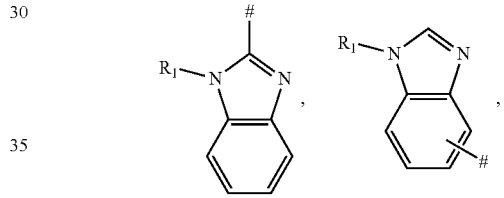

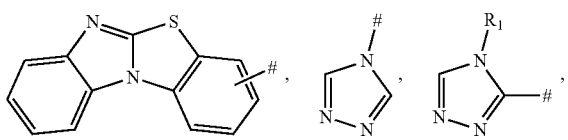

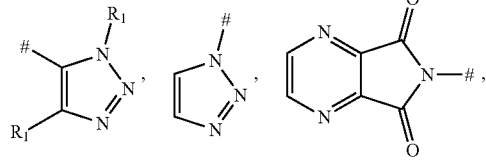

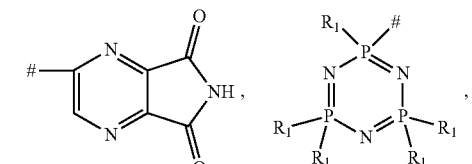

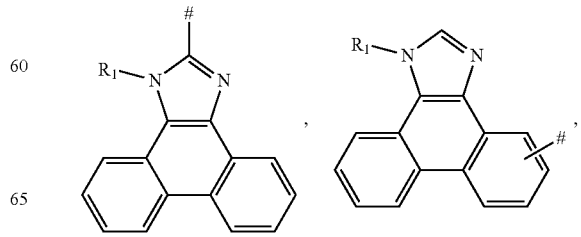

-continued
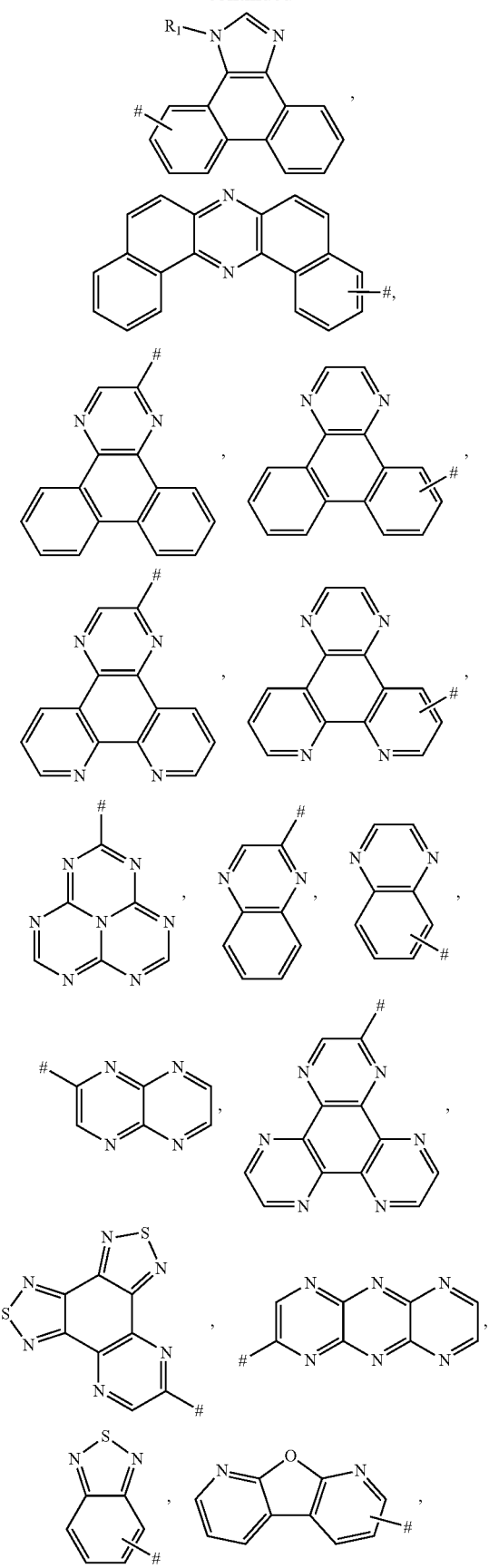
-continued
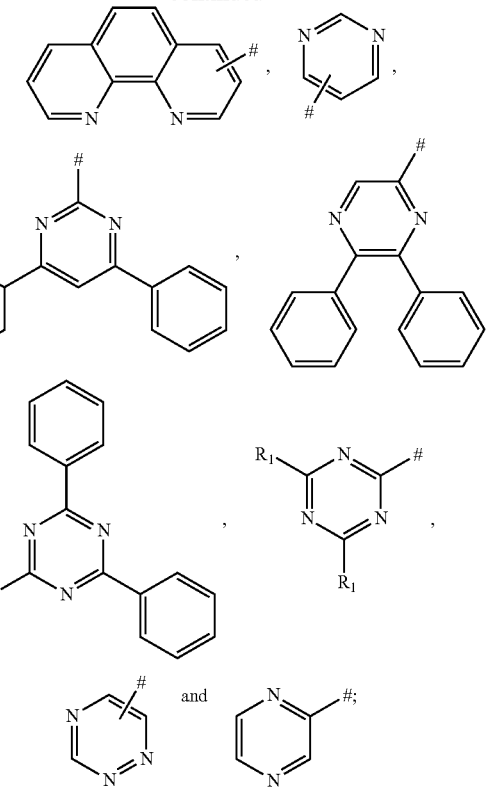
wherein $R_1$ is any one selected from the group consisting of $C_1$-$C_{20}$ alkyl, $C_1$-$C_{20}$ alkoxy, $C_6$-$C_{30}$ aryl and $C_2$-$C_{30}$ heteroaryl, and #represents a linkage position of groups.
4. The compound according to claim 1, wherein the sulfone-containing electron acceptor group is any one selected from the group consisting of the following groups:
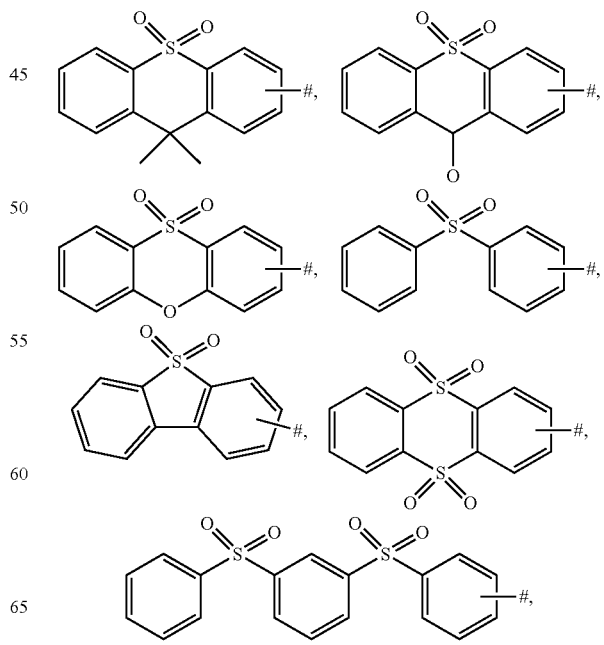

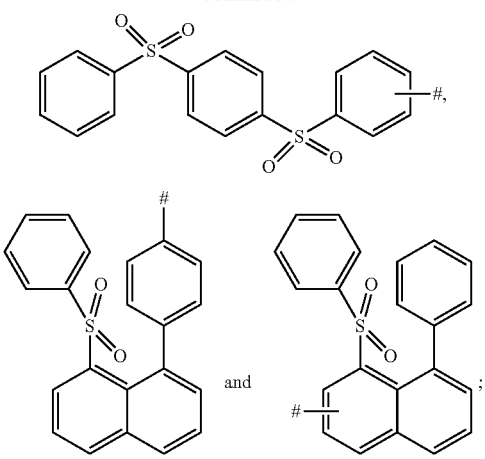
wherein #represents a linkage position of groups.
5. The compound according to claim 1, wherein the carbonyl-containing electron acceptor group is any one selected from the group consisting of the following groups:
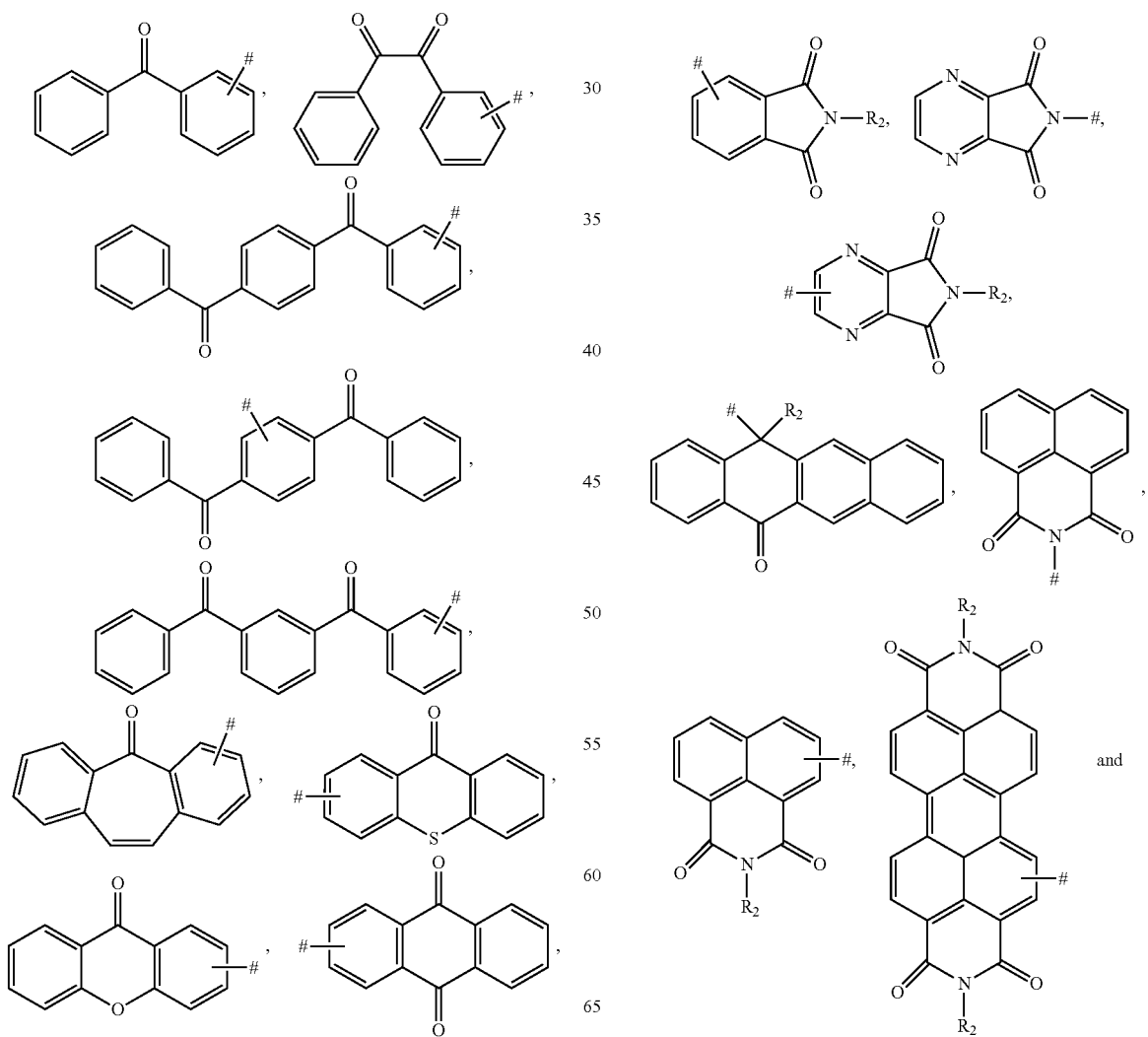
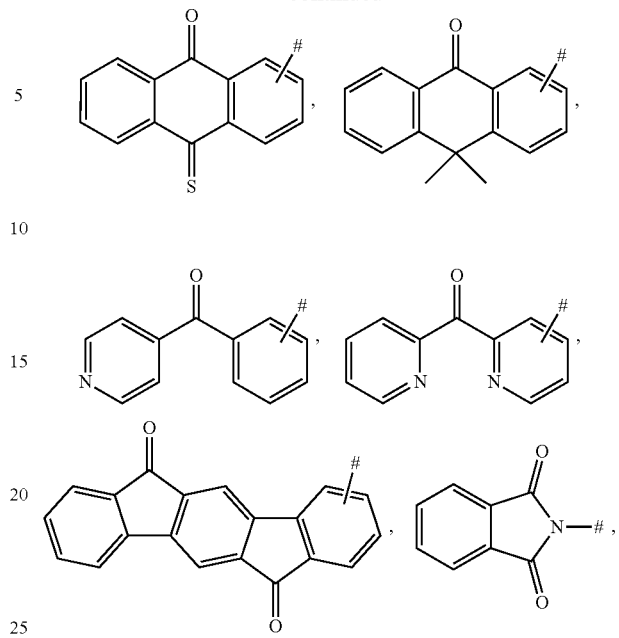

-continued

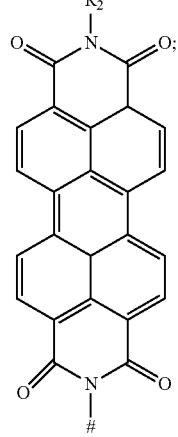

wherein $R_2$ is any one selected from the group consisting of $C_1$-$C_{20}$ alkyl, $C_1$-$C_{20}$ alkoxy, $C_6$-$C_{30}$ aryl and $C_2$-$C_{30}$ heteroaryl, and #represents a linkage position of groups.

6. The compound according to claim 1, wherein the phosphinyloxy-containing electron acceptor group is any one selected from the group consisting of the following groups:

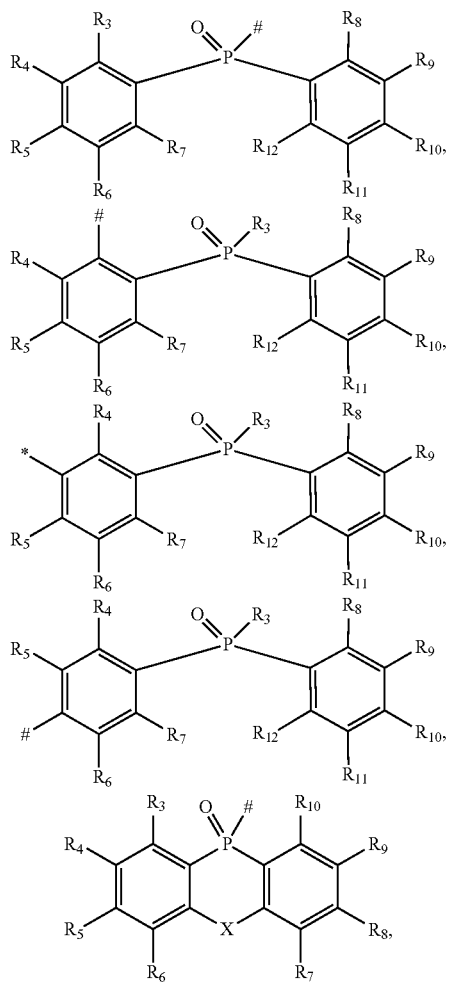

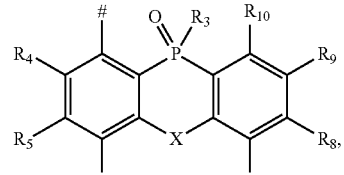

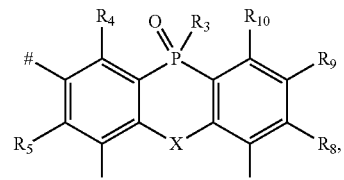

and

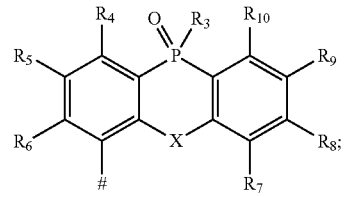

wherein X is O, S,

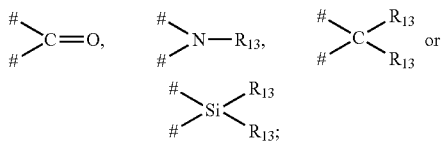

$R_3$ to $R_{12}$ are each independently any one selected from the group consisting of a hydrogen atom, $C_1$-$C_{20}$ alkyl, $C_1$-$C_{20}$ alkoxy, $C_6$-$C_{30}$ aryl and $C_2$-$C_{30}$ heteroaryl, Ria is any one selected from the group consisting of $C_6$-$C_{30}$ aryl and $C_2$-$C_{30}$ heteroaryl, and #represents a linkage position of groups.

7. The compound according to claim 1, wherein the boron-containing electron acceptor group is any one selected from the group consisting of the following groups:

-continued
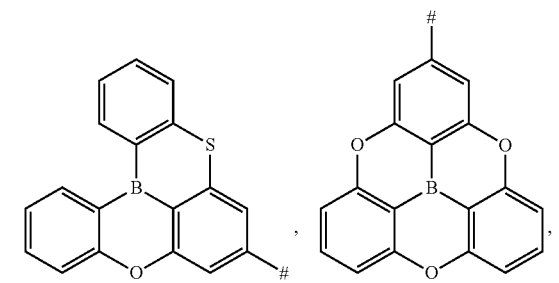
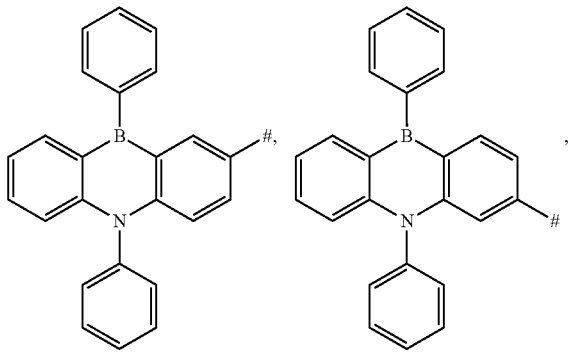
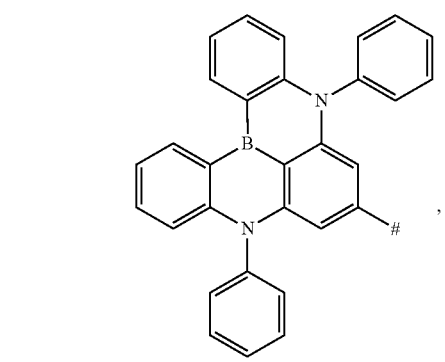
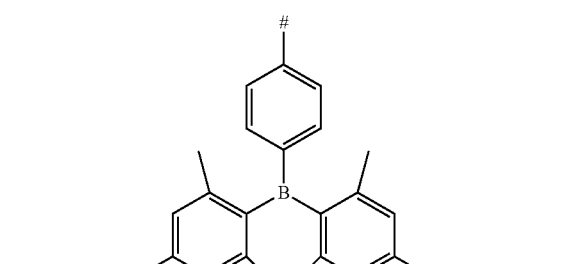
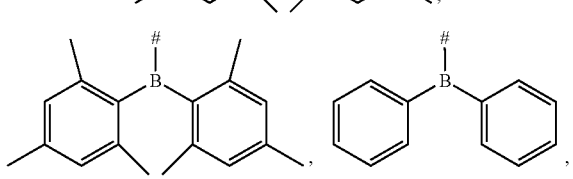
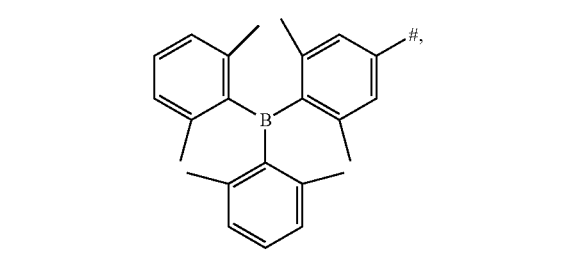
-continued
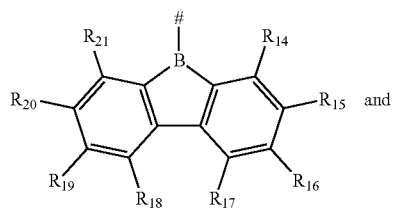
and
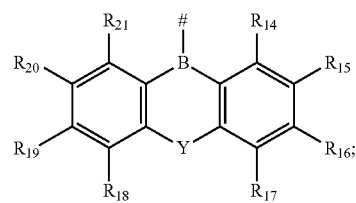
wherein Y is O, S,
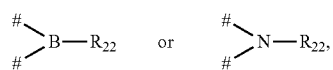
$R_{14}$ to $R_{22}$ are each independently any one selected from the group consisting of a hydrogen atom, $C_1$-$C_{20}$ alkyl, $C_1$-$C_{20}$ alkoxy, $C_6$-$C_{30}$ aryl and $C_2$-$C_{30}$ heteroaryl, and #represents a linkage position of groups.
8. A compound selected from the group consisting of the following compounds P1 to P97:
P1
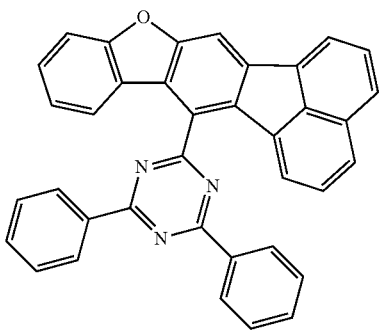
P2
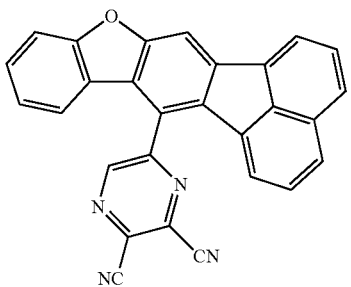

-continued
P3
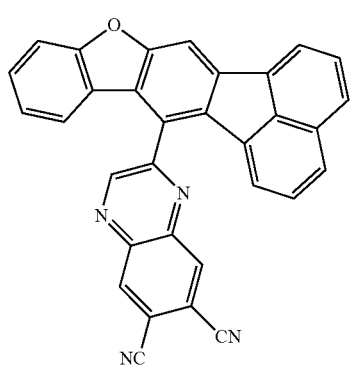
P4
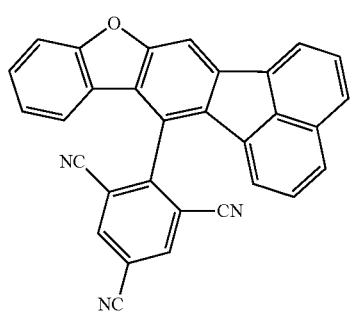
P5
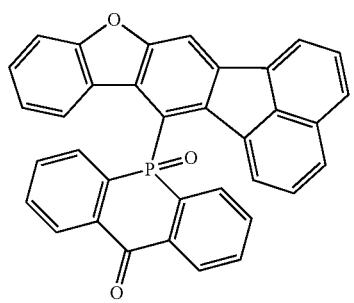
P6
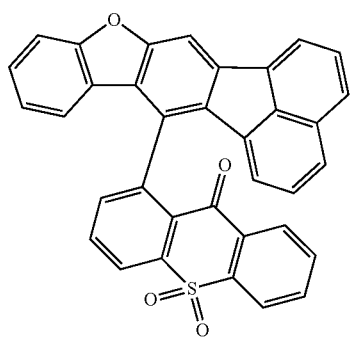
P7
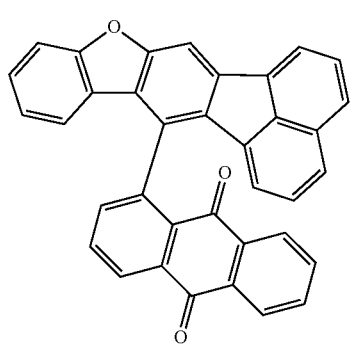
-continued
P8
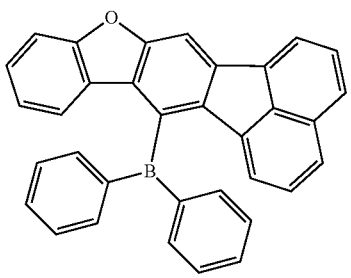
P9
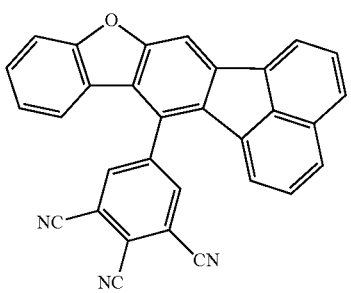
P10
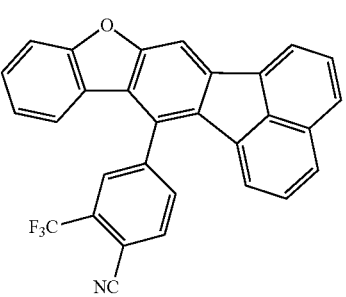
P11
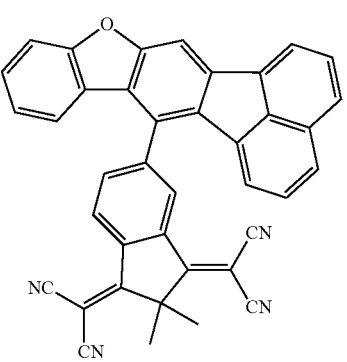
P12
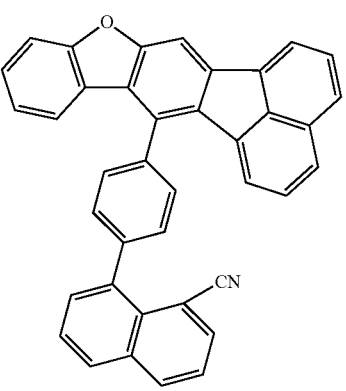

P13
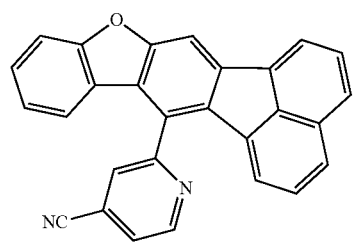
P14
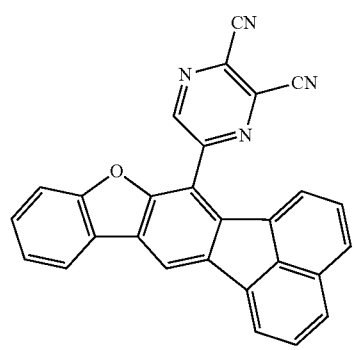
P15
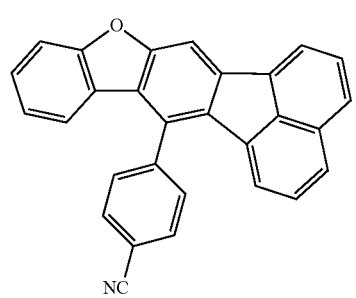
P16
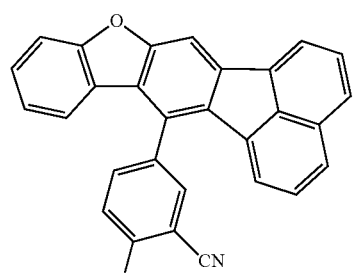
P17
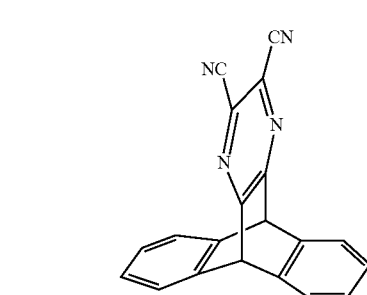
P18
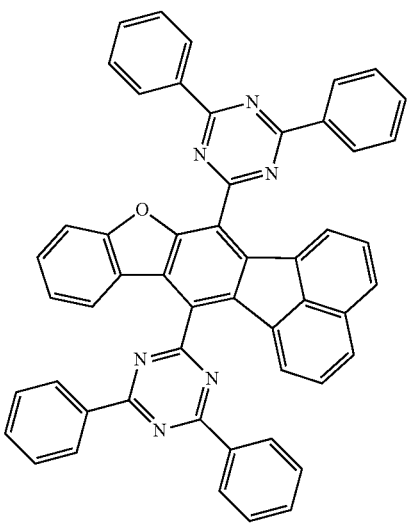
P19
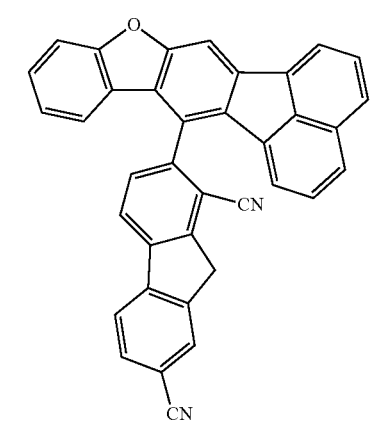
P20
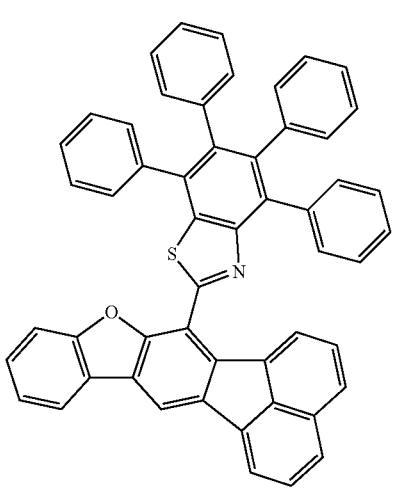

-continued
P21
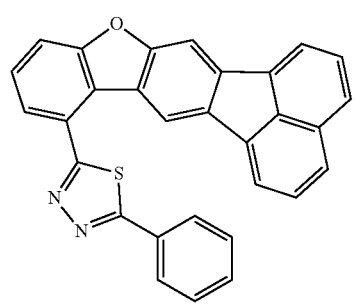
P22
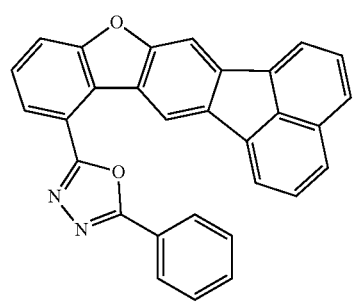
P23
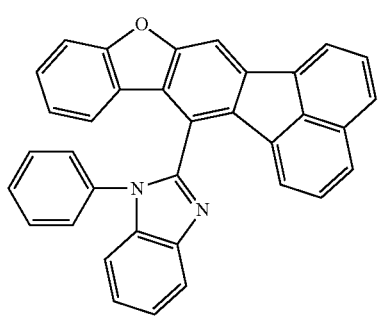
P24
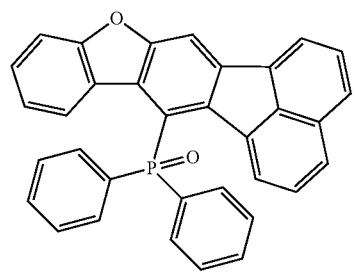
P25
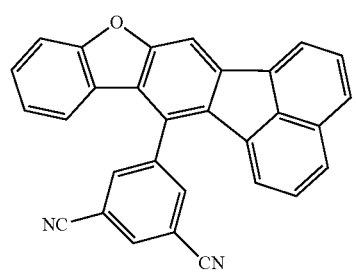
-continued
P26
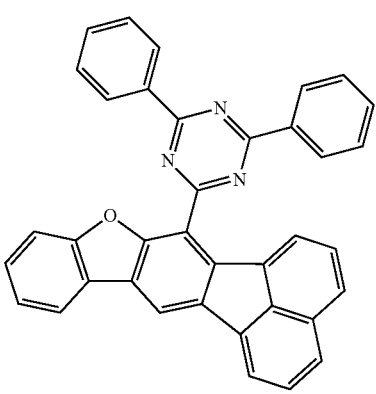
P27
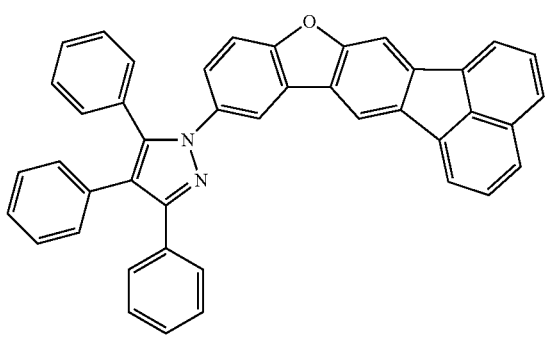
P28
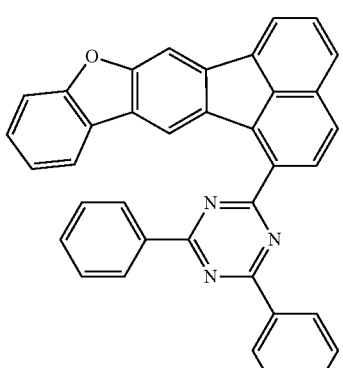
P29
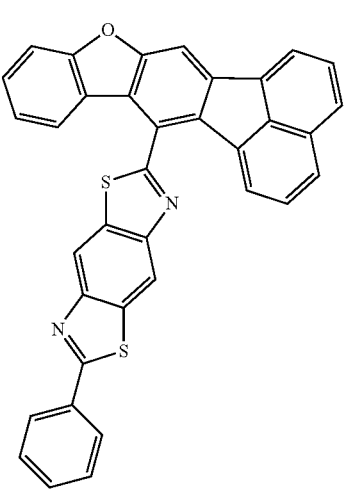

P30
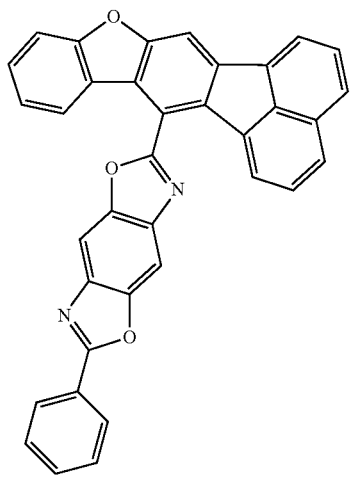
P31
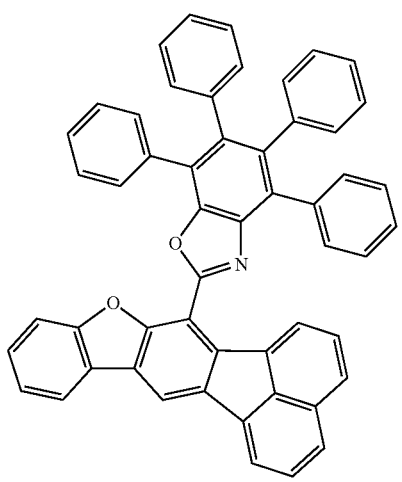
P32
P33
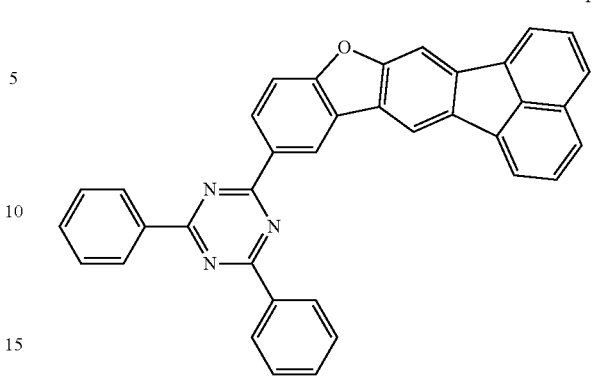
P34
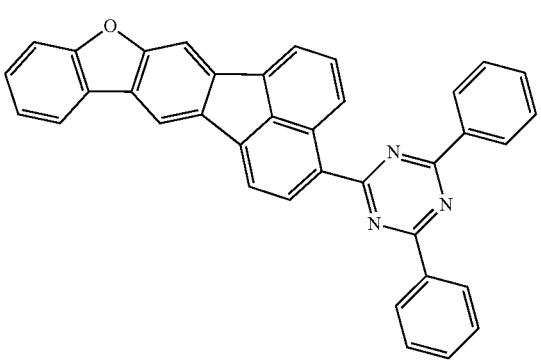
P35
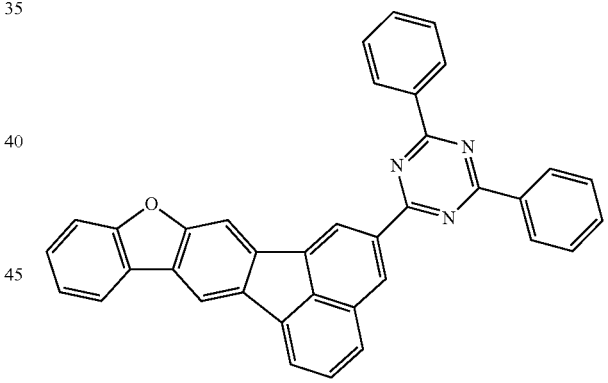
P36
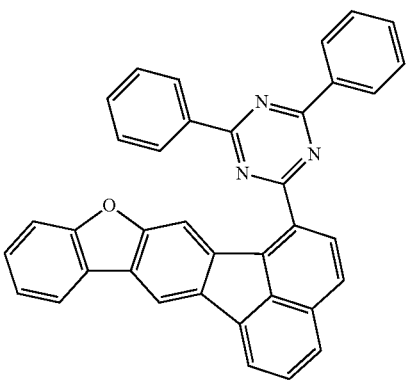

P37
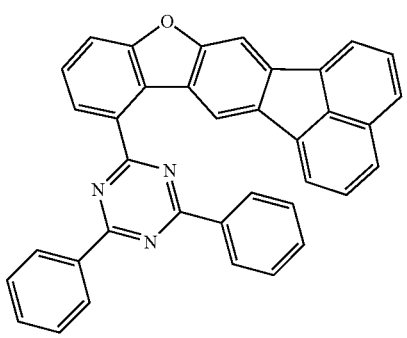
P38
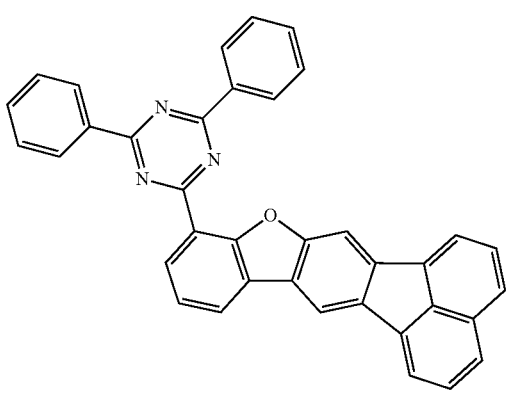
P39
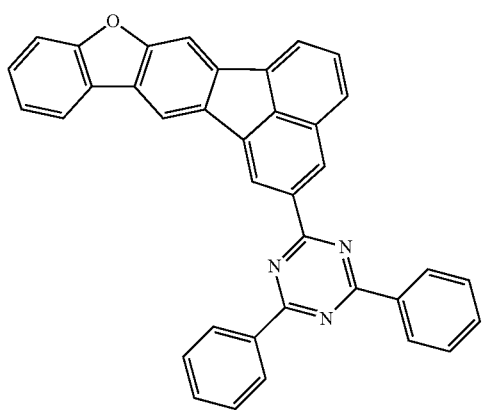
P44
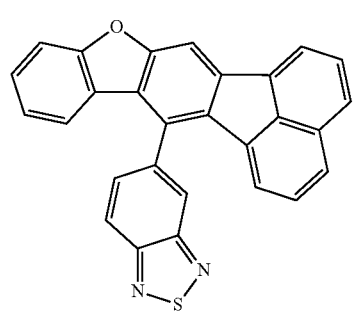
P45
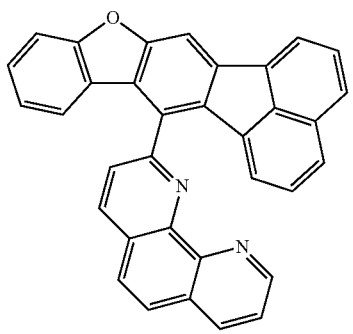
P46
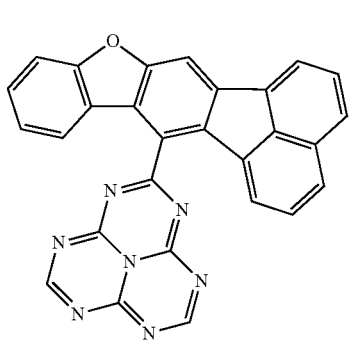
P47
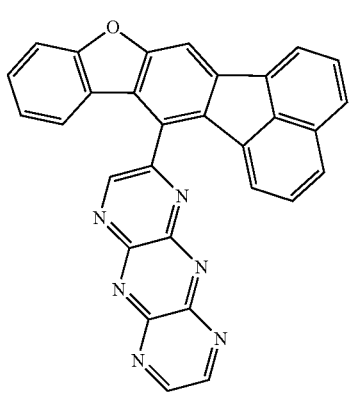
P48
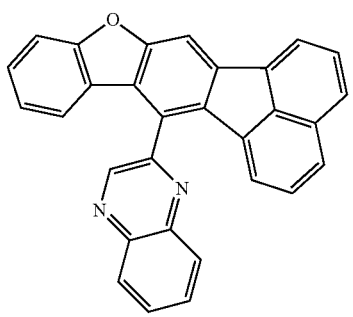

-continued
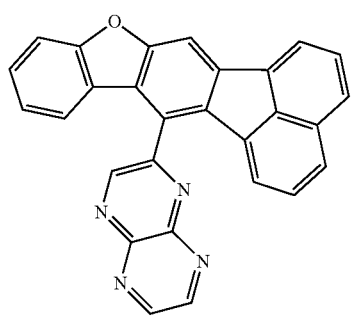
P49
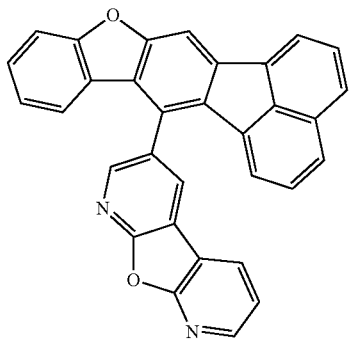
P53
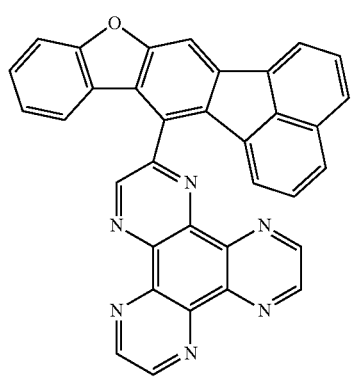
P50
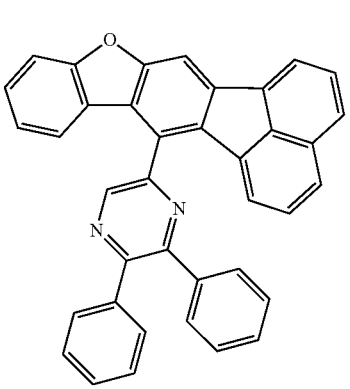
P54
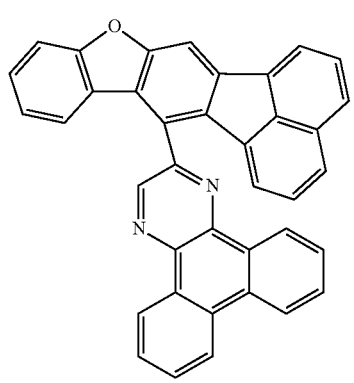
P51
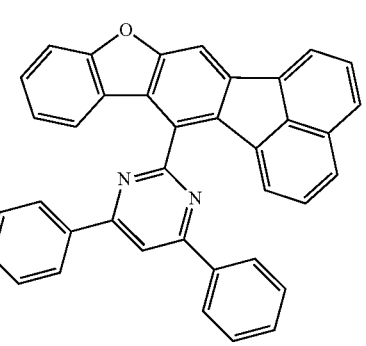
P55
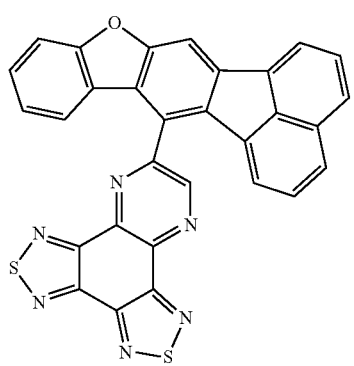
P52
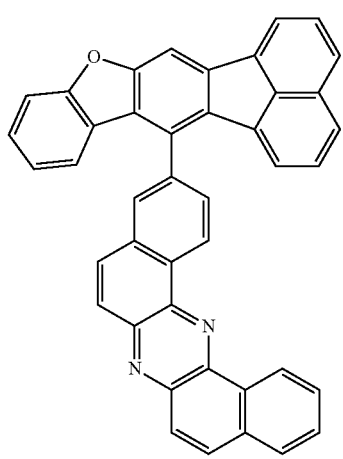
P56

P57
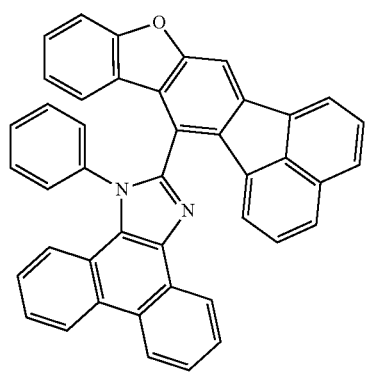
P58
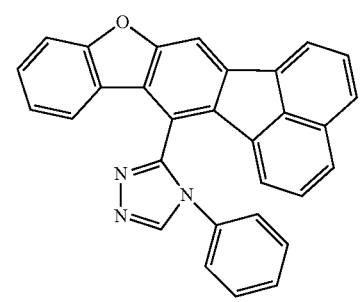
P59
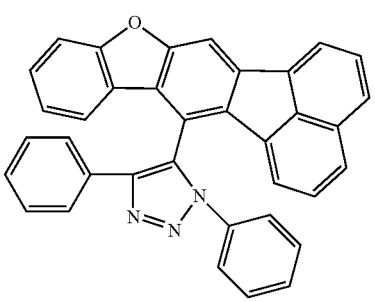
P60
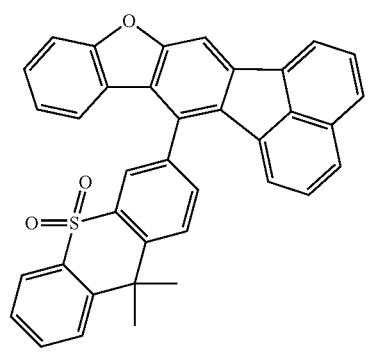
P61
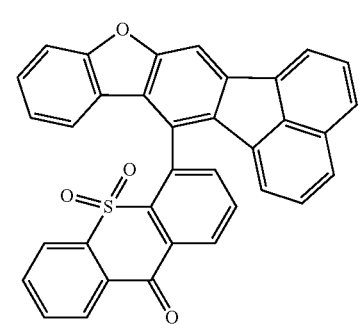
P62
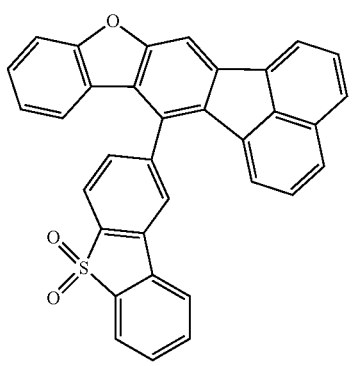
P63
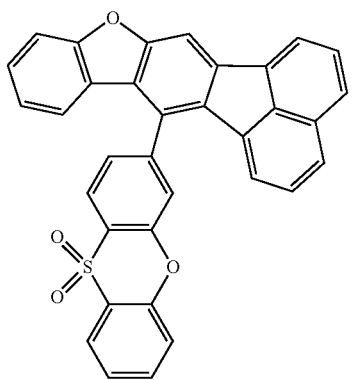
P64
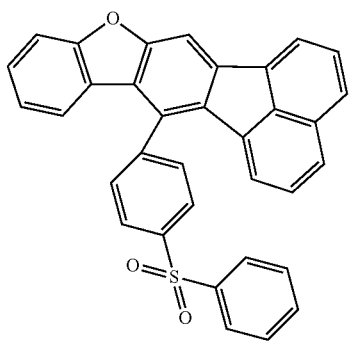
P65
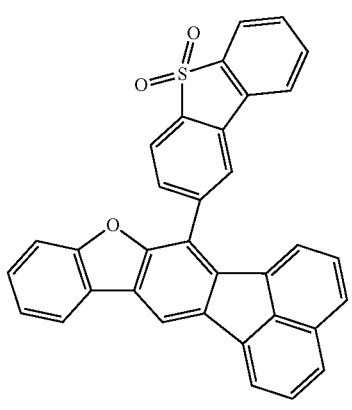

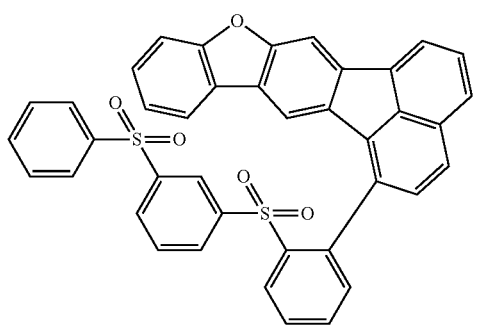
P66
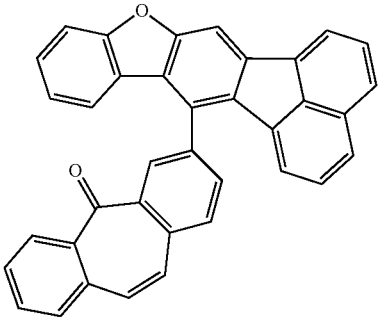
P70
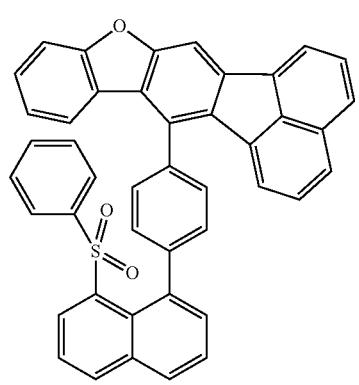
P67
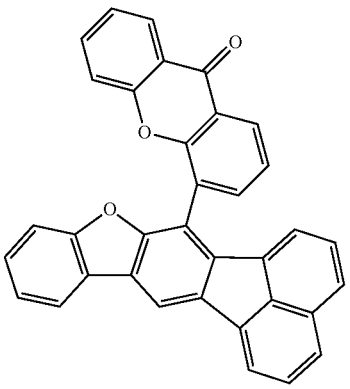
P71
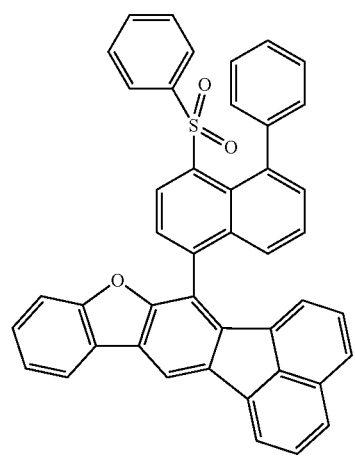
P68
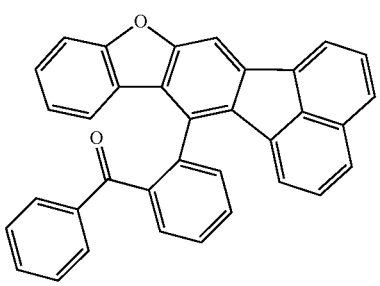
P72
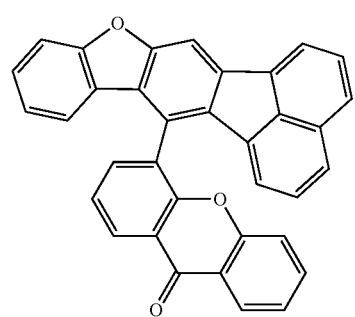
P69
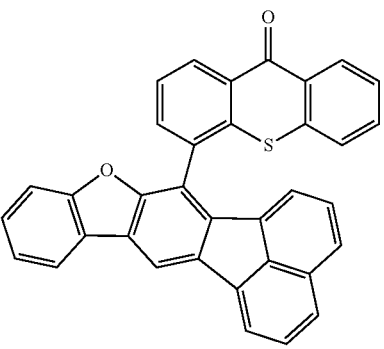
P73

P74
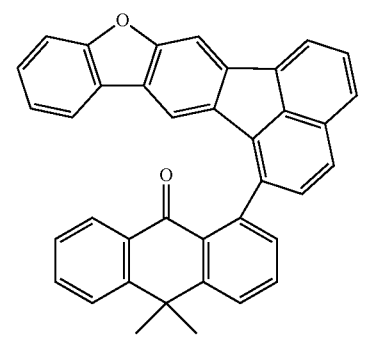
P75
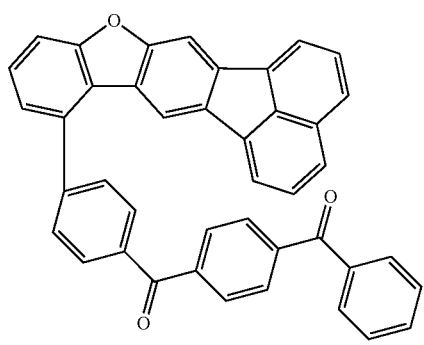
P76
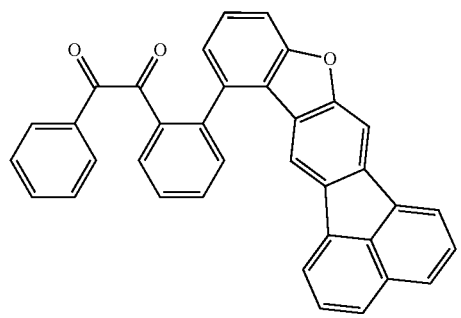
P77
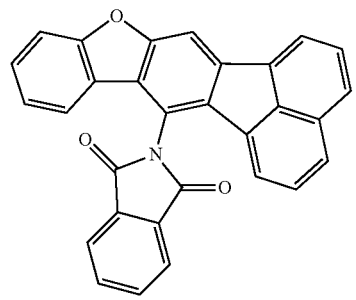
P78
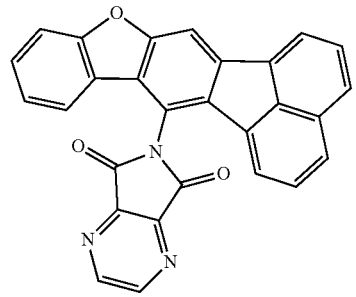
P79
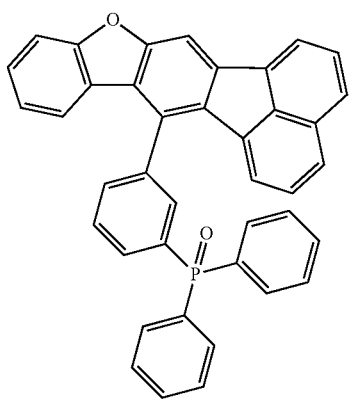
P80
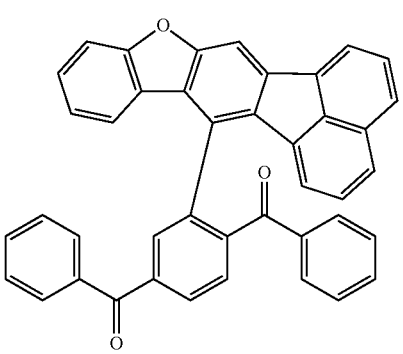
P81
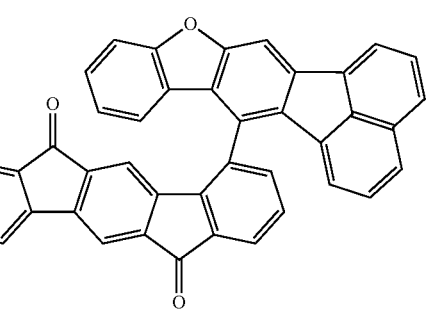
P82
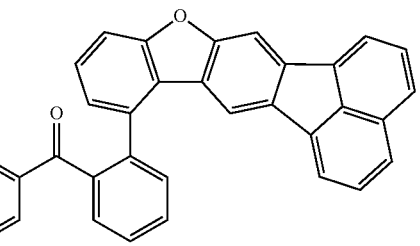
P83
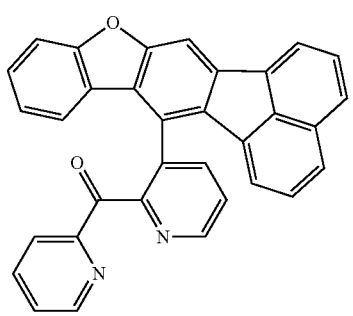

P84
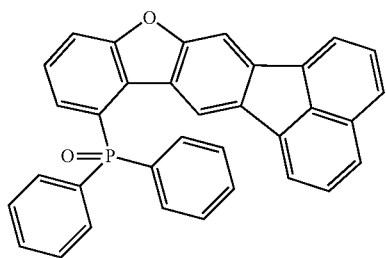
P85
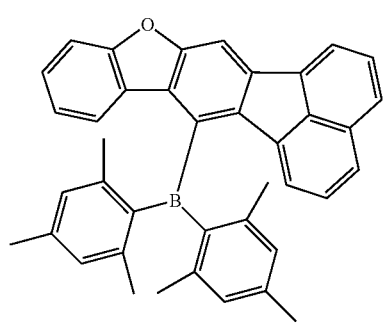
P86
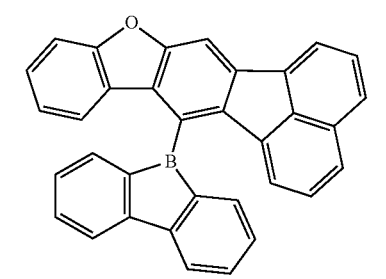
P87
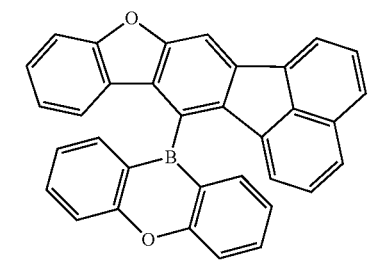
P88
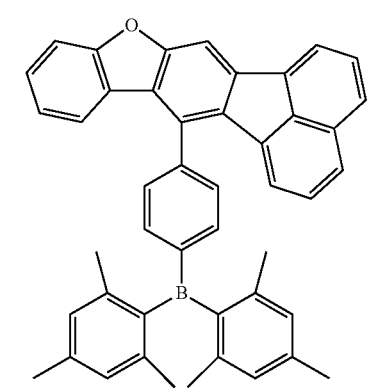
P89
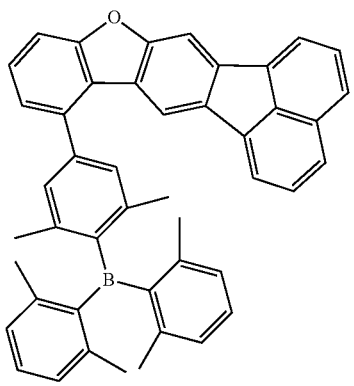
P90
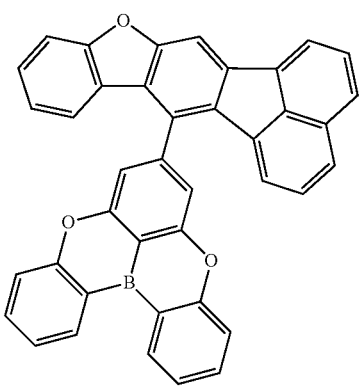
P91
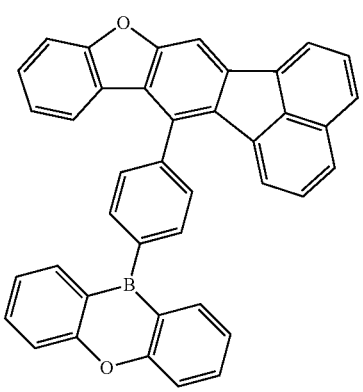
P92
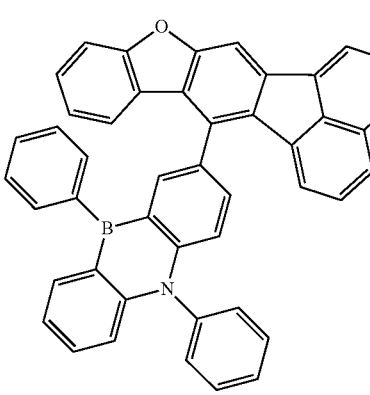

P93

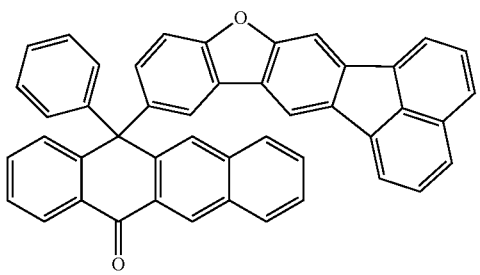

P94

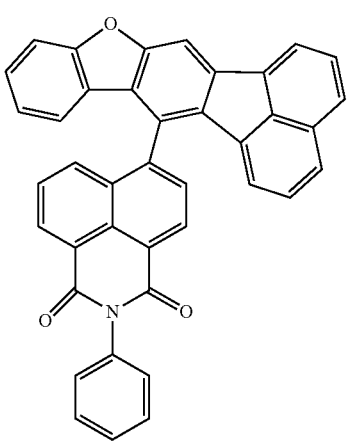

P95

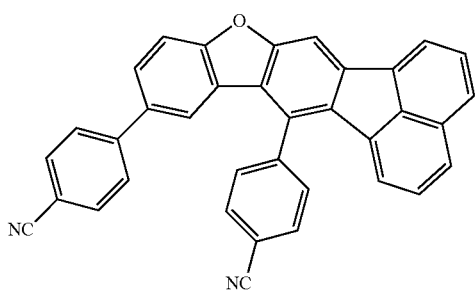

P96

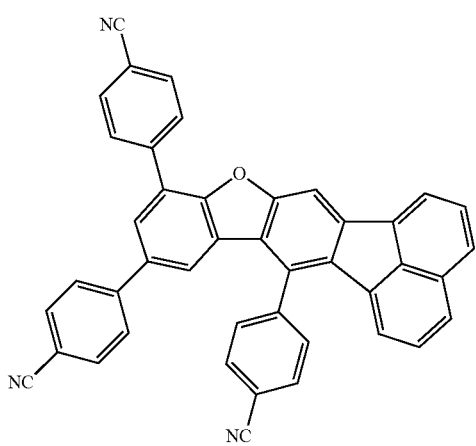

P97

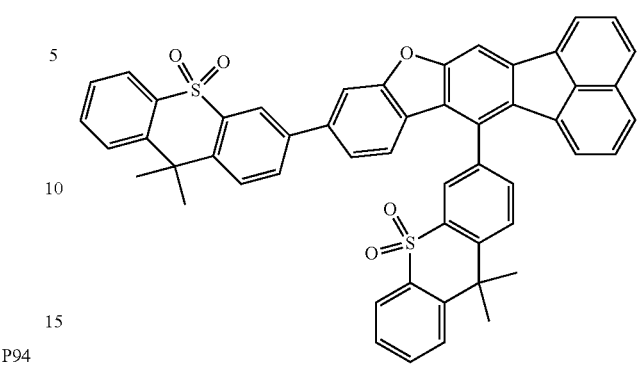

9. An organic electro-optical device comprising an anode, a cathode and at least one organic thin film layer located between the anode and the cathode;
wherein the at least one organic thin film layer is one selected from the group consisting of a hole injection layer, a hole transport layer, an electron blocking layer, a light emitting layer, a hole blocking layer, an electron transport layer, an electron injection layer, and a combination of at least two selected therefrom, and comprises a light emitting layer;
at least one of the organic thin film layers comprises at least one of the compounds having a structure represented by Formula II:

Formula II

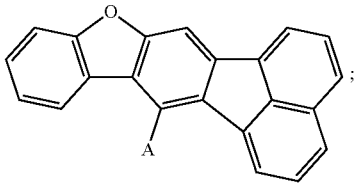

wherein A is any one selected from the group consisting of a cyano-containing electron acceptor group, a nitrogen heterocycle-containing electron acceptor group, a sulfone-containing electron acceptor group, a carbonyl-containing electron acceptor group, a phosphinyloxy-containing electron acceptor group and a boron-containing electron acceptor group.

10. The organic electro-optical device according to claim 9, wherein the organic electro-optical device comprises an anode, a hole injection layer, a hole transport layer, an electron blocking layer, a light emitting layer, a hole blocking layer, an electron transport layer, an electron injection layer and a cathode which are sequentially stacked.

11. The organic electro-optical device according to claim 9, wherein a material of the electron transport layer comprises one or more said compounds in Formular (II).

12. The organic electro-optical device according to claim 9, wherein the electron transport layer comprises a host material and a guest material, and the host material of the electron transport layer is one or more said compounds in Formular (II).

13. The organic electro-optical device according to claim 9, wherein a material of the hole blocking layer is one or more said compounds in Formular (II), and the lowest triplet energy level of a light emitting material of the light emitting layer is lower than the lowest triplet energy level of the compound.

* * * * *